(12) United States Patent
Choo et al.

(10) Patent No.: US 6,706,470 B2
(45) Date of Patent: Mar. 16, 2004

(54) GENE SWITCHES

(75) Inventors: Yen Choo, Cambridge (GB); Christopher Graeme Ullman, London (GB)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 09/995,973

(22) Filed: Nov. 28, 2001

(65) Prior Publication Data

US 2003/0024006 A1 Jan. 30, 2003

Related U.S. Application Data

(63) Continuation of application No. PCT/GB00/02071, filed on May 30, 2000.

(30) Foreign Application Priority Data

| May 28, 1999 | (GB) | 9912635 |
| Jan. 24, 2000 | (GB) | 0001578 |
| May 30, 2000 | (WO) | PCT/GB00/02071 |

(51) Int. Cl.$^7$ .......... C12Q 1/20; C12N 15/09; C07H 21/04; A01K 67/00
(52) U.S. Cl. .......... 435/5; 435/69.2; 435/325; 536/23.1; 800/8; 800/295
(58) Field of Search .......... 435/5, 6, 69.2, 435/325; 536/23.1; 800/8, 295

(56) References Cited

FOREIGN PATENT DOCUMENTS

| WO | WO 94/29442 | 12/1994 |
| WO | WO 96/06166 | 2/1996 |
| WO | WO 98/53057 | 11/1998 |

OTHER PUBLICATIONS

Gottesfeld et al. (1997) Nature 387:202–205.*
Dickinson et al. (April 30, 1999) J. Biol. Chem.274:12765–12773.*
Dickinson et al. (1998) Proc. Natl. Acad. Sci. U.S.A. 95:12890–12895.*
Dickinson et al., "Inhibition of RNA Polymerase II Transcription in Human Cells by Synthetic DNA–Binding Ligands," *PNAS* 95(22): 12890–12895 (1998).
Dickinson et al., "Inhibition of Ets–1 DNA Binding and Temary complex Formation Between Ets–1, NF–KappaB, and DNA by a Designed DNA–Binding Ligand," *Journal of Biological Chemistry* 274(8):12765–12773 (1999).
Gatz et al., "Stringent Repression and Homogenous De–Repression by Tetracycline of a Modified CaMV 355 Promoter in Intact Transgenic Tobacco Plants," *Plant Journal* 3(2):997–404 (1992).
Gottesfed et al, "Regulation of Gene Expression by Small Molecules," *Nature* 387(6629):202–205 (1997).
Weinmann et al., "Chimeric Transactivator Allows Tetracycline–Responsive Gene Expression in Whole Plants," *Plant Journal* 5(4):559–569 (1994).

* cited by examiner

*Primary Examiner*—James Ketter
*Assistant Examiner*—Daniel M. Sullivan
(74) *Attorney, Agent, or Firm*—Robins & Pasternak LLP

(57) ABSTRACT

Disclosed herein are methods and compositions relating to gene switches that use molecule capable of binding DNA sequences.

22 Claims, 3 Drawing Sheets

GENE SWITCHES

CROSS REFERENCE TO RELATED APPLICATIONS

This application claims priority under 35 U.S.C. §365(c) and 35 U.S.C. §120 as a continuation of PCT/GB00/02071 filed May 30, 2000 and priority under 35 U.S.C. §119/363 to United Kingdom applications Ser. No. 9912635.1 and 0001578.4.

FIELD OF THE INVENTION

This invention relates to molecular gene switches that use molecules capable of binding a specific DNA sequence in a ligand-dependent manner where the ligand itself is capable of binding DNA. Moreover, this invention relates to methods for the identification of said ligand-dependent DNA binding molecules.

BACKGROUND TO THE INVENTION

Gene switches are currently of great interest to those wishing to control timing and/or dosage of gene expression. Various gene switches have been developed in the prior art. Most of these prior art switches are derived from gene regulatory proteins. In these systems, the switching ligand binds to the protein, inducing a protein conformational change that affects DNA binding.

It is often the case that a gene's expression is affected by one or more different protein(s). Diverse proteins may influence expression of the same gene. Said protein(s) may be present in a first cell or cell type, but these protein(s) may be absent from a second cell or cell type. Therefore, a molecule which affects only a single known regulatory protein will not have any effect on the expression of the same gene in a cell where this particular regulatory protein is not expressed, or is otherwise sequestered. Thus, one of the difficulties of the prior art is that a protein-binding switching molecule will have no effect on the expression of a gene if the particular protein to which the switching molecule binds is not present.

Similarly, a gene's expression may be affected by numerous different proteins in different cells or cell types. A molecule which affects only a single known regulatory protein will not have any effect on the expression of the same gene in a cell in which its expression is controlled by a different protein or proteins. Therefore, one of the difficulties in the prior art is that a plurality of switching molecules may be required in order to modulate or switch the expression of a single gene.

Therefore, in order to effect switching of gene expression at a given DNA sequence, independently of the particular activator protein, it is desirable to target the DNA. Further, custom DNA binding proteins would benefit from switches; if these could be designed to interact with DNA, there would be a greater freedom in the design of said proteins.

There are numerous polypeptide modifications which are known to affect their interaction with a broad spectrum of molecules such as nucleic acids, polypeptides (both intra- and inter-molecularly) other macromolecular structures such as membranes, small molecules, ions, or other entities. Clearly, it is a problem that polypeptide modifications may compromise the binding of prior art switching molecules to their polypeptide targets.

The present invention seeks to overcome such difficulties.

Aspects of the present invention are set out in the claims and are described below.

SUMMARY OF THE INVENTION

In a first aspect, the present invention provides a method of selecting a gene switch, which gene switch comprises (i) a target DNA molecule; (ii) a DNA binding molecule which binds to the target DNA molecule in a manner modulatable by a DNA binding ligand; and (iii) the DNA binding ligand, which method comprises:

(a) contacting one or more candidate target DNA molecule(s) with one or more candidate DNA binding molecules, in the presence of one or more DNA binding ligands, wherein at least one of the candidate DNA binding molecules comprises a non-naturally occurring DNA binding domain;

(b) selecting a complex comprising a candidate target DNA, a DNA binding molecule and a DNA binding ligand;

(c) isolating and/or identifying the unknown components of the complex;

(d) comparing the binding of the DNA binding molecule component of the complex to the target DNA component of the complex in the presence and absence of the DNA binding ligand component of the complex; and (e) selecting complexes where said binding differs in the presence and absence of the DNA binding ligand component.

Preferably the DNA binding molecules are provided as a plurality of DNA binding molecules, more preferably as a library of DNA binding molecules. Where only one DNA binding molecule is included in the screen, the DNA binding molecule comprises a non-naturally occurring DNA binding domain. The term "a non-naturally occurring DNA binding domain" means that the DNA binding domain does not occur in nature, even as part of a larger molecule, and has been obtained by deliberate mutagensis procedures or de novo design techniques.

Preferably the target DNA is provided as a plurality of DNA sequences, more preferably as a library of DNA sequences, said sequences being related to one another by sequence homology.

In one embodiment, a plurality of candidate DNA binding ligands are used, in which case is preferred to use one target DNA.

Typically one of the components isolated and/or identified in step (c) is a DNA binding ligand component or a DNA binding molecule component.

In a preferred embodiment of the first aspect of the invention, the selected DNA binding molecule component has a higher affinity for the target DNA in the presence of the DNA binding ligand component than in the absence of the DNA binding ligand component.

Alternatively, the selected DNA binding molecule component has a higher affinity for the target DNA in the absence of the DNA binding ligand component than in the presence of the DNA binding ligand component.

In a highly preferred embodiment, the candidate DNA binding molecules are provided as a phage display library.

The method of the present invention may be used to select a DNA binding molecule which binds to a target DNA molecule in a manner modulatable by a DNA binding ligand.

The method of the present invention may also be used to select a target DNA to which binds a DNA binding molecule in a manner modulatable by a DNA binding ligand.

The method of the present invention may also further be used to select a DNA binding ligand that modulates binding of a DNA binding molecule to a target DNA.

Generally, the DNA binding ligand and the DNA binding molecule are different

In a preferred aspect of the invention, said candidate molecules are polypeptides. In a more preferred embodiment, said candidate molecules are polypeptides at least partly derived from transcription factors. In an even more preferred embodiment, said candidate molecules are derived from zinc finger transcription factors.

Advantageously, the candidate DNA binding molecules are provided as a phage display library.

In a preferred aspect of the invention, the DNA binding ligand is selected from Distamycin A, Actinomycin D and echinomycin.

In another aspect, the invention relates a gene switch comprising (i) a target DNA molecule; (ii) a DNA binding molecule which binds to the target DNA molecule in a manner modulatable by a DNA binding ligand; and (iii) the DNA binding ligand. In particular, the present invention relates to DNA binding molecules and/or DNA binding ligands and/or target DNA obtainable by the methods disclosed herein.

The present invention also provides a method for engineering a novel class of gene switches in which a DNA binding ligand affects or modulates the interaction of a DNA binding molecule (for example phage displayed polypeptide), with its target DNA. In a preferred aspect, the present invention relates to the selection of DNA binding polypeptides which recognise a particular DNA sequence or structure. Preferably, said method may include selection of phage displayed polypeptides that bind a DNA target in the presence or absence of one or more DNA binding ligands. Of the phage displayed polypeptides which are selected under these conditions, some may bind the DNA with higher affinity in the presence of ligand, whereas others may bind the DNA with higher affinity in the absence of ligand.

The gene switches and components thereof can be used in methods of regulating gene expression. Accordingly, the present invention also provides a method of modulating the expression of one or more genes, said method comprising administering a DNA binding molecule and DNA binding ligand selected according to the method of the invention to a cell wherein the regulatory sequences of said genes comprise a target DNA selected according to the method of the invention.

The present invention also provides a method of modulating the expression of one or more nucleotide sequences of interest in a host cell which host cell comprises a nucleic acid sequence capable of directing the expression of a DNA binding molecule and a target DNA sequence to which the DNA binding molecule binds in a manner modulatable by a DNA binding ligand which method comprises administering said DNA binding ligand to the cell and wherein the DNA binding molecule is heterologous to the host cell.

Preferably the host cell is a plant cell. More preferably the plant cell is part of a plant and the target sequence is part of a regulatory sequence to which the nucleotide sequence of interest is operably linked, said regulatory sequence being preferentially active in the male or female organs of the plant.

In a further aspect there is provided the use of a DNA binding molecule selected by the method of the invention in a method of regulating transcription from a DNA sequence comprising a target DNA to which the DNA binding molecule binds in a manner modulatable by a DNA binding ligand.

Also provided is the use of a DNA binding ligand selected by the method of the invention in a method of regulating transcription from a DNA sequence comprising a target DNA to which a DNA binding molecule binds in a manner modulatable by the DNA binding ligand.

Also provided is the use of a target DNA selected by the method of the invention in a method of regulating transcription from a DNA sequence comprising the target DNA to which a DNA binding molecule binds in a manner modulatable by a DNA binding ligand.

In another aspect, the present invention provides a non human transgenic organism comprising a target DNA sequence and a nucleic acid sequence capable of directing the expression of a DNA binding molecule which binds to the target DNA in a manner modulatable by a DNA binding ligand wherein the target DNA sequence and/or nucleic acid sequence are heterologous to the organism.

Preferably the transgenic non-human organism is a plant.

DETAILED DESCRIPTION OF THE INVENTION

Definitions

Figure 1:
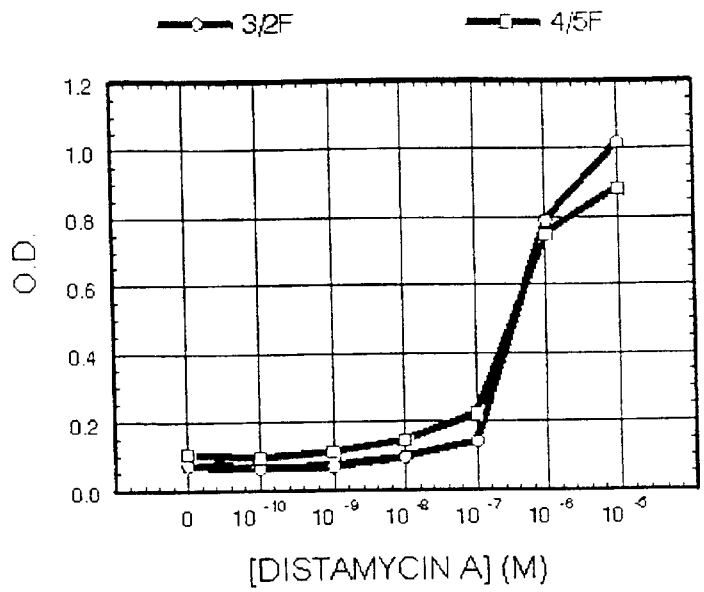
FIG. 1 shows a graph of the effect of Distamycin A concentration on binding of two different phage (clone 3 (3/2F) and clone 4 (4/5F) to the DNA sequence AAAAAG-GCG. In this case, the small molecule causes phage binding to DNA.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference), chemical methods, pharmaceutical formulations and delivery and treatment of patients.

The term 'modulatable by' is used to indicate that binding of the DNA binding molecule to the DNA can be modulated or affected by the DNA binding ligand. In other words, the DNA binding ligand can modulate, affect, regulate, adjust, alter, or vary the binding of the DNA binding molecule to the DNA.

The term 'isolating' in the context of the invention, refers to the act of removing one or more components or molecules from a sample of candidate molecules which are used in the methods disclosed herein.

The term 'complex' is used to describe an association between a DNA and one or more molecules as defined herein.

The term "gene switch" is used herein to describe a multiple component system comprising (i) a target DNA molecule; (ii) a DNA binding molecule which binds to the target DNA molecule in a manner modulatable by a DNA binding ligand; and (iii) the DNA binding ligand. The DNA binding molecule may or may not comprise a transcriptional effector domain, especially when part of the assay procedure. However, since ultimately the gene switch will be used to regulate transcription from one or more promoters, the DNA binding molecule may need to be modified to include a transcriptional activator or repressor domain, if one is not already present.

The terms "DNA binding molecule", "DNA binding ligand" and "target DNA" are used extensively herein. However other types of nucleic acids other than DNA may be relevant. Consequently, it is intended that in general the above terms can be replaced with the terms "nucleic acid binding molecule", "nucleic acid binding ligand" and "target nucleic acid", respectively. Nucleic acids will in general be RNA or DNA, double stranded or single stranded. RNA is preferably at least partially double-stranded in the context of the present invention. However, in a preferred aspect of the invention, references to "DNA" mean deoxyribonucleic acid in a literal sense.

A. DNA binding molecules

The term 'DNA binding molecule' includes any molecule which is capable of binding or associating with DNA. This binding or association may be via covalent bonding, via ionic bonding, via hydrogen bonding, via Van-der-Waals bonding, or via any other type of reversible or irreversible association.

The term 'molecule' is used herein to refer to any atom, ion, molecule, macromolecule (for example polypeptide), or combination of such entities. The term 'ligand' is used interchangeably with the term 'molecule'. Molecules according the invention may be free in solution, or may be partially or fully immobilised. They may be present as discrete entities, or may be complexed with other molecules. Preferably, molecules according to the invention include polypeptides displayed on the surface of bacteriophage particles. More preferably, molecules according to the invention include libraries of polypeptides presented as integral parts of the envelope proteins on the outer surface of bacteriophage particles. Methods for the production of libraries encoding randomised polypeptides are known in the art and may be applied in the present invention. Randomisation may be total, or partial; in the case of partial randomisation, the selected codons preferably encode options for amino acids, and not for stop codons.

The term 'candidate DNA binding molecules' is used to describe any one or more molecule(s) as defined above which may or may not be capable of binding DNA. The capability of said molecules to bind DNA may or may not be modulatable by a DNA binding ligand. The latter of these properties may be investigated by the methods of this invention. Preferably, candidate DNA binding molecules comprise a plurality of, or a library of polypeptides. More preferably, these polypeptides are, or are derived from, DNA binding proteins such as DNA repair enzymes, polymerases, recombinases, methylases, restriction enzymes, replication factors, histones, or DNA binding structural proteins such as chromosomal scaffold proteins; even more preferably said polypeptides are derived from transcription factors. 'Derived from' means that the candidate DNA binding molecules preferably comprise one or more of; transcription factors, fragment(s) of transcription factors, sequences homologous to transcription factors, or polypeptides which have been fully or partially randomised from a starting sequence which is a transcription factor, a fragment of a transcription factor, or homologous to a transcription factor. Most preferably, candidate DNA binding molecules comprise polypeptides which are at least 40% homologous, more preferably at least 60% homologous, even more preferably at least 75% homologous or even more, for example 85%, or 90%, or even more than 95% homologous to one or more transcription factors, using one of the homology calculation algorithms defined below.

Candidate DNA binding molecules may comprise, among other things. DNA binding part(s) of any protein(s), for example zinc finger transcription factors, Zif268, ATF family transcription factors, ATF1, ATF2, bZIP proteins, CHOP, NF-κB, TATA binding protein (TBP), MDM, c-jun, elk, serum response factor (SRF), ternary complex factor (TCF); KRÜPPEL, Odd Skipped, even skipped and other *D. melanogaster* transcription factors; yeast transcription factors such as GCN4, the GAL family of galactose-inducible transcription factors; bacterial transcription factors or repressors such as lacI$^q$, or fragments or derivatives thereof. Derivatives would be considered by a person skilled in the art to be functionally and/or structurally related to the molecule(s) from which they are derived, for example through sequence homology of at least 40%.

The candidate DNA binding molecules may be non-randomised polypeptides, for example 'wild-type' or allelic variants of naturally occurring polypeptides, or may be specific mutant(s), or may be wholly or partially randomised polypeptides, preferably structurally related to DNA binding proteins as described herein.

In a highly preferred embodiment, these polypeptide candidate DNA binding molecules are displayed on the surface of bacteriophage particles, and are preferably partially randomised zinc-finger type transcription factors, preferably retaining at least 40% homology (as described herein) to zinc-finger type transcription factors.

In some cases, sequence homology may be considered in relation to structurally important residues, or those residues which are known or suspected of being evolutionarily conserved. In such instances, residues known to be variable or non-essential for a particular structural conformation may be discounted from the homology calculation. For example, as explained herein, zinc fingers are known to have certain residues which are important for the formation of the three-dimensional zinc finger structure. In these cases, homology may be considered over about seven of said important amino acid residues amongst approximately thirty residues which may comprise the whole finger structure.

As used herein, the term homology may refer to structural homology. Structural homology may be estimated by comparing the structural RMS deviation of the main part of the carbon atom backbone of two or more molecules. Preferably, the molecules may be considered structurally homologous if the deviation is 5 Å or less, preferably 3 Å or less, more preferably 1.5 Å or less. Structurally homologous molecules will not necessarily show significant sequence homology.

Candidate DNA binding molecules, as defined above, may be prescreened prior to being tested in the methods of the invention using routine assays known in art for determining the binding of molecules to nucleic acids so as to eliminate molecules that do not bind DNA. For example, a candidate DNA binding molecule, preferably a library of candidate DNA binding molecules, are contacted with nucleic acid and binding determined. The nucleic acids may for example be labelled with a detectable label, such as a filuorophore/flurochrome, such that after a wash step binding can be determined easily, for example by monitoring fluorescence. Other methods for measuring binding to DNA are set out in section E. Below.

The nucleic acid with which the candidate binding ligands are contacted may be non-specific nucleic acids, such as a random oligonucleotide library or sonicated genomic DNA and the like. Alternatively, a specific sequence may be used or partially randomised library of sequences.

Preferably, the DNA binding molecules of the invention may bind the target nucleic acid with different affinity in the presence or in the absence of ligand. The binding to the nucleic acid may be enhanced by the presence of the ligand (i.e. bind with a higher affinity in the presence of ligand), or may be reduced in the presence of ligand (i.e. bind with a lower affinity in the presence of ligand). In the case where association of the DNA binding molecule(s) with the target nucleic acid is enhanced by the presence of ligand, said association may be additive with the binding of the ligand, or may be synergistic with the binding of the ligand, or may affect the binding in another way. If the binding is synergistic with the binding of the ligand, said binding may be either wholly or partly dependent on the presence of the ligand. Preferably, the characteristics of binding may be such that the DNA binding molecule(s) may be eluted by addition of an excess of the DNA binding ligand.

DNA binding molecules according to the invention are preferably polypeptide sequences, optionally encoded by nucleic acid sequences. Fragments, mutants, alleles and other derivatives of the molecules of the invention preferably retain substantial homology with said sequence(s). As used herein, "homology" means that the two entities share sufficient characteristics for the skilled person to determine that they are similar. Preferably, homology is used to refer to sequence identity. Thus, the derivatives of said DNA binding molecules of the invention preferably retain substantial sequence identity with said molecules.

In the context of the present invention, a homologous sequence is taken to include any sequence which is at least 60, 70, 80 or 90% identical, preferably at least 95 or 98% identical over at least 5, preferably 8, 10, 15, 20, 30, 40 or even more residues or bases with the molecules (ie. the sequences thereof) of the invention, for example as shown in the sequence listing herein. In particular, homology should typically be considered with respect to those regions of the molecule(s) which may be known to be functionally important rather than non-essential neighbouring sequences. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

DNA binding molecules according to the invention may include any atom, ion, molecule, macromolecule (for example polypeptide), or combination of such entities that are capable of binding to nucleic acids, such as DNA. Advantageously, molecules according to the invention may include families of polypeptides with known or suspected nucleic acid binding motifs. These may include for example zinc finger proteins (see below). Molecules according to the invention may also include helix-turn-helix proteins, homeodomains, leucine zipper proteins, helix-loop-helix proteins or β-sheet motifs which are well known to a person skilled in the art.

According to the invention, DNA binding motifs of one or more known or suspected nucleic acid binding polypeptide (s) may advantageously be randomised, in order to provide libraries of candidate nucleic acid binding molecules.

Crystal structures may advantageously be used in selecting or predicting the relevant DNA binding regions of nucleic acid binding proteins by methods known in the art.

DNA binding regions of proteins within the same structural family are often conserved or homologous to one another, for example zinc finger α-helices, the leucine zipper basic region, homeodomain helix 3.

General considerations and rules governing the binding of several polypeptide families to nucleic acids are set out in the literature, e.g. in (Suzuki et al., 1994:PNAS vol 91 pp 12357–61). Nucleic acid binding criteria for zinc fingers as preferred DNA binding molecules according to the present invention are set out in this application (see above).

It is also envisaged that the methods of the present invention could be advantageously applied to the selection of ligand-modulatable DNA binding molecules from other families of transcription factors, for example from the helix-turn-helix (HTH) family and/or from the probe helix (PH) family, and/or from the C4 Zinc-binding family (which includes the hormone receptor (HR) family), from the Gal4 family, from the c-myb family, from other zinc finger families, or from any other family of DNA binding proteins known to one skilled in the art.

One or more polypeptides from one or more of these families could be advantageously randomised to provide a library of candidate molecules for use in the methods of the invention. Preferably, the amino acid residues known to be important for nucleic acid binding could be randomised. However, it may be desirable to randomise other regions of the DNA binding molecule since alterations to the amino acid sequence outside of those elements of secondary structure that present amino acids that contact the DNA are likely to cause conformational changes that may affect the DNA binding properties of the molecule.

For example, randomisation may involve alteration of zinc finger polypeptides, said alteration being accomplished at the DNA or protein level. Mutagenesis and screening of zinc finger polypeptides may be achieved by any suitable means. Preferably, the mutagenesis is performed at the nucleic acid level, for example by synthesising novel genes encoding mutant polypeptides and expressing these to obtain a variety of different proteins. Alternatively, existing genes can themselves be mutated, such as by site-directed or random mutagenesis, in order to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Preferably, the commercially available Altered Site II Mutagenesis System (Promega) may be employed, according to the manufacturer's instructions.

Randomisation of the zinc finger binding motifs is preferably directed to those amino acid residues where the code provided herein gives a choice of residues (see below). For example, positions +1, +5 and +8 are advantageously randomised, whilst preferably avoiding hydrophobic amino acids; positions involved in binding to the nucleic acid, notably −1, +2, +3 and +6, may be randomised also, preferably within the choices provided by the rules of the present invention.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pII of bacteriophage m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431–436; Smith, (1985) Science 228:1315–1317; and McCafferty et al., (1990) Nature 348:552–554; all incorporated herein by reference. Vector systems and kits for phage display are available commercially, for example from Pharmacia.

Specific peptide ligands such as zinc finger polypeptides may moreover be selected for binding to targets by affinity selection using large libraries of peptides linked to the C-terminus of the lac repressor LacI (Cull et al., (1992) Proc Natl Acad Sci USA, 89, 1865–9). When expressed in *E. coli* the repressor protein physically links the ligand to the encoding plasmid by binding to a lac operator sequence on the plasmid.

An entirely in vitro polysome display system has also been reported (Mattheakis et al., (1994) Proc Natl Acad Sci USA, 91, 9022–6) in which nascent peptides are physically attached via the ribosome to the RNA which encodes them. Furthermore, polypeptides may be partitioned in physical compartments for example wells of an in vitro dish, or subcellular compartments, or in small fluid particles or droplets such as emulsions: further teachings on this topic may be found in Griffith et al., (see WO 99/02671).

A library for use in the invention may be randomised at those positions for which choices are given in the rules of the first embodiment of the present invention. The rules set forth above allow the person of ordinary skill in the art to make informed choices concerning the desired codon usage at the given positions.

The recognition helix of PH family polypeptides contains conserved Arg/Lys residues which are important structural elements involved in the binding of phosphates in the nucleic acid. Base specificity is attributed to amino acids 1, 4, 5 and 8 of the helix. These residues could be advantageously varied, for example amino acid 1 could be selected from Asn, Asp, His, Val, Ile to provide the possibility of binding to A, C, G, or T. Similarly, amino acid 4 could be selected from Asn, Asp, His, Val, Ile, Gln, Glu, Arg, Lys, Met, or Leu to provide the possibility of binding to A, C, G or T. Preferably, the rules laid out in (Suzuki et al., 1994: PNAS vol 91 pp 12357–61) would be used in order to randomise those amino acids which affect interaction of the molecule with the nucleic acid, whether in a base specific manner, or via binding to the phosphate backbone, thereby producing a library of candidate nucleic acid binding molecules for use in the methods of the invention.

Similarly, polypeptide molecules of the helix-turn-helix family could be randomised to produce a library of candidate molecules, at least some of which may preferably be capable of binding nucleic acid in a ligand-dependent manner when used in the methods of the present invention. In particular, amino acids 1, 2, 5 and 6 are known to be conserved and function in base-specific nucleic acid binding in HTH motifs. Therefore, at least amino acids 1, 2, 5 or 6 would preferably be randomised so as to produce molecules for use according to the present invention. More preferably, amino acids 1, 5 and 6 could be selected from Asn, Asp, His, Val, Ile, Glu, Gln, Arg, Met, Lys or Leu, and amino acid 2 could be selected from from Asn, Asp, His, Val, Ile, Glu, Gln, Arg, Met, Lys, Leu, Cys, Ser, Thr, or Ala.

Another family of transcription factors which may be advantageously employed in the methods of the current invention are the C4 family which includes hormone receptor type transcription factors. It is envisaged that polypeptides of this family could advantageously be used to provide candidate molecules for use in selecting nucleic acid binding molecules whose association with nucleic acid is modulatable by a nucleic acid binding ligand. Amino acids 1, 4, 5 and 9 of the C4 motif are known to be involved in contacting the DNA, and therefore these residues would preferably be altered to provide a plurality of different molecules which may bind DNA in a ligand dependent manner. Preferably, amino acids 1 and 5 could be selected from from Asn, Asp, His, Val, Ile, Glu, Gln, Arg, Met, Lys or Leu, and amino acids 4 and 9 could be selected from Gln, Glu, Arg, Lys. Leu or Met.

Particularly preferred examples of DNA binding molecules are Cys2-His2 zinc finger binding proteins which, as is well known in the art, bind to target nucleic acid sequences via α-helical zinc metal atom co-ordinated binding motifs known as zinc fingers. Each zinc finger in a zinc finger nucleic acid binding protein is responsible for determining binding to a nucleic acid triplet, or an overlapping quadruplet, in a nucleic acid binding sequence. Preferably, there are 2 or more zinc fingers, for example 2, 3, 4, 5 or 6 zinc fingers, in each binding protein. Advantageously, there are 3 zinc fingers in each zinc finger binding protein.

Thus, in one embodiment, the invention provides a method for preparing a DNA binding polypeptide of the Cys2-His2 zinc finger class capable of binding to a target DNA sequence, wherein binding is via a zinc finger DNA binding motif of the polypeptide, and wherein said binding is modulatable by a DNA binding ligand.

All of the DNA binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger, "++" interactions do not operate.

The present invention is in one aspect concerned with the production of what are essentially artificial DNA binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues or mimetics of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the − strand of the nucleic acid, since it is this strand which is aligned 3' to 5'. These conventions are followed in the nomenclature used herein. It should be noted, however, that in nature certain fingers, such as finger 4 of the protein GLI, bind to the + strand of nucleic acid: see Suzuki et al., (1994) NAR 22:3397–3405 and Pavletich and Pabo, (1993) Science 261:1701–1707. The incorporation of such fingers into DNA binding molecules according to the invention is envisaged.

The present invention may be integrated with the rules set forth for zinc finger polypeptide design in our copending European or PCT patent applications having publication numbers; WO 98/53057, WO 98/53060, WO 98/53058, WO 98/53059, describe improved techniques for designing zinc finger polypeptides capable of binding desired nucleic acid sequences. In combination with selection procedures, such as phage display, set forth for example in WO 96/06166, these techniques enable the production of zinc finger polypeptides capable of recognising practically any desired sequence.

In a preferred aspect, therefore, the invention provides a method for preparing a DNA binding polypeptide of the Cys2-His2 zinc finger class capable of binding to a target DNA sequence, wherein said binding is modulatable by a DNA binding ligand, and wherein binding to each base of the triplet by an α-helical zinc finger DNA binding motif in the polypeptide is determined as follows:

a) if the 5' base in the triplet is G, then position +6 in the α-helix is Arg and/or position ++2 is Asp;

b) if the 5' base in the triplet is A, then position +6 in the α-helix is Gln or Glu and ++2 is not Asp;

c) if the 5' base in the triplet is T, then position +6 in the α-helix is Ser or Thr and position ++2 is Asp; or position +6 is a hydrophobic amino acid other than Ala;

d) if the 5' base in the triplet is C, then position +6 in the α-helix may be any amino acid, provided that position ++2 in the α-helix is not Asp;

e) if the central base in the triplet is G, then position +3 in the α-helix is His;

f) if the central base in the triplet is A, then position +3 in the α-helix is Asn;

g) if the central base in the triplet is T, then position +3 in the α-helix is Ala, Ser, Ile, Leu, Thr or Val: provided that if it is Ala, then one of the residues at −1 or +6 is a small residue;

h) if the central base in the triplet is 5-meC, then position +3 in the α-helix is Ala, Ser, Ile, Leu, Thr or Val; provided that if it is Ala, then one of the residues at −1 or +6 is a small residue;

i) if the 3' base in the triplet is G, then position −1 in the α-helix is Arg;

j) if the 3' base in the triplet is A, then position −1 in the α-helix is Gln and position +2 is Ala;

k) if the 3' base in the triplet is T, then position −1 in the α-helix is Asn; or position −1 is Gln and position +2 is Ser;

l) if the 3' base in the triplet is C, then position −1 in the α-helix is Asp and Position +1 is Arg; where the central residue of a target triplet is C, the use of Asp at position +3 of a zinc finger polypeptide allows preferential binding to C over 5-meC.

The foregoing represents a set of rules which permits the design of a zinc finger binding protein specific for any given target DNA sequence.

A zinc finger binding motif is a structure well known to those in the art and defined in, for example, Miller et al., (1985) EMBO J. 4:1609–1614; Berg (1988) PNAS (USA) 85:99–102; Lee et al., (1989) Science 245:635–637; see International patent applications WO 96/06166 and WO 96132475, corresponding to U.S. Ser. No. 08/422,107, incorporated herein by reference.

In general, a preferred zinc finger framework has the structure:

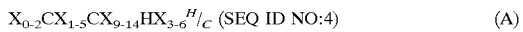

where X is any amino acid, and the numbers in subscript indicate the possible numbers of residues represented by X.

In a preferred aspect of the present invention, zinc finger nucleic acid binding motifs may be represented as motifs having the following primary structure:

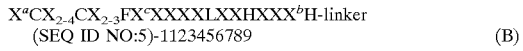

wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example it is known that the second His residue may be replaced by Cys (Krizek et al., (1991) J. Am. Chem. Soc. 113:4518–4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix coordinated by a zinc atom which contacts four Cys or His residues, does not alter. As used herein, structures (A) and (B) above are taken as an exemplary structure representing all zinc finger structures of the Cys2-His2 type.

Preferably, $X^a$ is $^F/_Y$-X or P-$^F/_Y$-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I. Preferably, $X^c$ is S or T.

Preferably, $X_{2-3}$ is G-K-A, G-K-C, G-K-S or G-K-G. However, departures from the preferred residues are possible, for example in the form of M-R-N or M-R.

Preferably, the linker is T-G-E-K (SEQ ID NO:6) or T-G-E-K-P (SEQ ID NO:7).

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position ++2 is any amino acid, and preferably serine, save where its nature is dictated by its role as a ++2 amino acid for an N-terminal zinc finger in the same nucleic acid binding molecule.

In a most preferred aspect, therefore, bringing together the above, the invention allows the definition of every residue in a zinc finger DNA binding motif which will bind specifically to a given target DNA triplet.

The code provided by the present invention is not entirely rigid; certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target DNA triplet.

Preferably, however, the number of possibilities may be significantly reduced. For example, the non-critical residues +1, +5 and +8 may be occupied by the residues Lys, Thr and Gln respectively as a default option. In the case of the other choices, for example, the first-given option may be employed as a default. Thus, the code according to the present invention allows the design of a single, defined polypeptide (a "default" polypeptide) which will bind to its target triplet.

In a further aspect of the present invention, there is provided a method for preparing a DNA binding protein of the Cys2-His2 zinc finger class capable of binding to a target DNA sequence in a manner modulatable by a DNA binding ligand, comprising the steps of:

a) selecting a model zinc finger domain from the group consisting of naturally occurring zinc fingers and consensus zinc fingers; and b) mutating at least one of positions −1, +3, +6 (and ++2) of the finger as required by a method according to the present invention.

In general, naturally occurring zinc fingers may be selected from those fingers for which the DNA binding specificity is known. For example, these may be the fingers for which a crystal structure has been resolved: namely Zif 268 (Elrod-Erickson et al., (1996) Structure 4:1171–1180), GLI (Pavletich and Pabo, (1993) Science 261:1701–1707), Tramtrack (Fairall et al., (1993) Nature 366:483–487) and YY1 (Houbaviy et al., (1996) PNAS (USA) 93:3577–13582).

The naturally occurring zinc finger 2 in Zif 268 makes an excellent starting point from which to engineer a zinc finger and is preferred.

Consensus zinc finger structures may be prepared by comparing the sequences of known zinc fingers, irrespective of whether their binding domain is known. Preferably, the consensus structure is selected from the group consisting of the consensus structure P YKCPECGKSFSQKS-DLVKHQRTHTG (SEQ ID NO:8), and the consensus structure PYKCSECGKAFSQKSNLTRHQRIHTGEKP (SEQ ID NO:9).

The consensuses are derived from the consensus provided by Krizek et al., (1991) J. Am. Chem. Soc. 113: 4518–4523 and from Jacobs, (1993) PhD thesis, University of Cambridge, UK. In both cases, the linker sequences described above for joining two zinc finger motifs together, namely TGEK (SEQ ID NO:6) or TGEKP (SEQ ID NO:7) can be formed on the ends of the consensus. Thus, a P may be removed where necessary, or, in the case of the consensus terminating TG, EK (P) can be added.

When the nucleic acid specificity of the model finger selected is known, the mutation of the finger in order to modify its specificity to bind to the target DNA may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/DNA interface in order to assist in residue selection.

In a second embodiment, the invention provides a method for producing a zinc finger polypeptide capable of binding to a target DNA sequence, wherein said binding is modulatable by a DNA binding ligand, comprising:

a) providing a nucleic acid library encoding a repertoire of zinc finger polypeptides, the nucleic acid members of the library being at least partially randomised at one or more of the positions encoding residues −1, 2, 3 and 6 of the α-helix of the zinc finger polypeptides;

b) displaying the library in a selection system and screening it against a target DNA sequence;

c) isolating the nucleic acid members of the library encoding zinc finger polypeptides capable of binding to the target sequence in the presence/absence of DNA binding ligand;

d) selecting those members of the library isolated in (c) which bind the target nucleic acid sequence with different affinities in the presence and absence of the DNA binding ligand.

Methods for the production of libraries encoding randomised polypeptides are known in the art and may be applied in the present invention. Randomisation may be total, or partial; in the case of partial randomisation, the selected codons preferably encode options for amino acids as set forth in the rules above.

Zinc finger polypeptides may be designed which specifically bind to nucleic acids incorporating the base U, in preference to the equivalent base T.

In a further preferred aspect, the invention comprises a method for producing a zinc finger polypeptide capable of binding to a target DNA sequence, wherein said binding is modulatable by a DNA binding ligand, comprising:

a) providing a nucleic acid library encoding a repertoire of zinc finger polypeptides each possessing more than one zinc fingers, the nucleic acid members of the library being at least partially randomised at one or more of the positions encoding residues −1, 2, 3 and 6 of the α-helix in a first zinc finger and at one or more of the positions encoding residues −1, 2, 3 and 6 of the α-helix in a further zinc finger of the zinc finger polypeptides;

b) displaying the library in a selection system and screening it against a target DNA sequence;

c) assessing the affinity of the DNA binding molecules for the target DNA in the presence and absence of the DNA binding ligand, and d) isolating the nucleic acid members of the library encoding zinc finger polypeptides capable of binding to the target sequence with different affinities in the presence and absence of DNA binding ligand.

In this aspect, the invention encompasses library technology described in our copending International patent application WO 98/53057, incorporated herein by reference in its entirety. WO 98/53057 describes the production of zinc finger polypeptide libraries in which each individual zinc finger polypeptide comprises more than one, for example two or three, zinc fingers; and wherein within each polypeptide partial randomisation occurs in at least two zinc fingers.

This allows for the selection of the "overlap" specificity, wherein within each triplet, the choice of residue for binding to the third nucleotide (read 3' to 5' on the + strand) is influenced by the residue present at position +2 on the subsequent zinc finger, which displays cross-strand specificity in binding. The selection of zinc finger polypeptides incorporating cross-strand specificity of adjacent zinc fingers enables the selection of nucleic acid binding proteins more quickly, and/or with a higher degree of specificity than is otherwise possible.

Zinc finger binding motifs designed according to the invention may be combined into nucleic acid binding polypeptide molecules having a multiplicity of zinc fingers. Preferably, the proteins have at least two zinc fingers. In nature, zinc finger binding proteins commonly have at least three zinc fingers, although two-zinc finger proteins such as Tramtrack are known. The presence of at least three zinc fingers is preferred. Nucleic acid binding proteins may be constructed by joining the required fingers end to end, N-terminus to C-terminus. Preferably, this is effected by joining together the relevant nucleic acid sequences which encode the zinc fingers to produce a composite nucleic acid coding sequence encoding the entire binding protein. The invention therefore provides a method for producing a DNA binding protein as defined above, wherein the DNA binding protein is constructed by recombinant DNA technology, the method comprising the steps of:

a) preparing a nucleic acid coding sequence encoding two or more zinc finger binding motifs as defined above, placed N-terminus to C-terminus;

b) inserting the nucleic acid sequence into a suitable expression vector; and c) expressing the nucleic acid sequence in a host organism in order to obtain the DNA binding protein.

A "leader" peptide may be added to the N-terminal finger. Preferably, the leader peptide is MAEEKP (SEQ ID NO:10).

B. Nucleic Acid Vectors Encoding DNA Binding Proteins

A nucleic acid encoding the DNA binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector.

Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2µ plasmid origin is suitable for yeast, and various viral origins (e.g. SV40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast, mammalian or plant cells even though it is not capable of replicating independently of the host cell chromosome. DNA may also be replicated by insertion into the host genome. However, the recovery of genomic DNA encoding the DNA binding protein is more complex than that of episomally replicated vector because restriction enzyme digestion is required to excise DNA binding protein DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins. e.g. ampicillin, neomycin, methotrexate or tetracycline, complement auxotrophic deficiencies, or supply critical nutrients not available from complex media.

Selectable markers which may be used in fungal cells, for example yeast cells, include wild-type genes which complement auxotrophic defects in for example the Uracil (eg. URA3 gene), Lysine (eg. LYS2 gene), Adenine (eg. ADE2 gene), Methionine (eg. MET3 gene), Histidine (eg. HIS3 gene), Tryptophan (eg. TRP1 gene), Leucine (eg. LEU2 gene) or other metabolic pathways. In addition, counter-selection methods are well known in the art. These enable genes to be selected against by the action of a chemical precursor which is harmless unless converted to a toxic product by the action of one or more gene(s). Examples of these include; 5-fluoro-orotic acid, which is converted to a toxic compound by the action of the URA3 gene product; α-amino-adipic acid, which is converted to a toxic compound by the LYS2 gene product; allyl alcohol, which is converted to a toxic compound by alcohol dehydrogenase activity as encoded by the ADH genes, or any other suitable selective regime known to those skilled in the art. Other selective markers are based on the expression of a gene in a fungus such as yeast which overcomes the metabolic arrest induced by, or toxicity of, a chemical entity which may be added to the growth medium or otherwise presented to the cells. Examples of these may include the KAN gene(s) which confer resistance to antibiotics such as G-418, the HIS3 gene which confers resistance to 3-amino-triazole, or the ADH2 gene which can confer resistance to heavy metal ions such as cadmium, or any other suitable genes which confer resistance to toxic or growth arresting regimes.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Suitable selectable markers for mammalian cells are those that enable the identification of cells competent to take up DNA binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the DNA binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to nucleic acid encoding DNA binding protein. Such a promoter may be inducible or constitutive. The promoters are operably linked to DNA encoding the DNA binding protein by removing the promoter from the source DNA by restriction enzyme digestion and inserting the isolated promoter sequence into the vector. Both the native DNA binding protein promoter sequence and many heterologous promoters may be used to direct amplification and/or expression of DNA binding protein encoding DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding DNA binding protein, using linkers or adapters to supply any required restriction sites. Promoters for use in bacterial systems will also generally contain a Shine-Delgarno sequence operably linked to the DNA encoding the DNA binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the E. coli BL21(DE3) host strain, used in conjunction with pET vectors, the T7 RNA polymerase is produced from the β-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int-phage such as the CE6 phage which is commercially available (Novagen, Madison, USA). Other vectors include vectors containing the lambda PL promoter such as PLEX (Invitrogen, NL), vectors containing the trc promoters such as pTrcHisXpressTm (Invitrogen) or pTrc99 (Pharmacia Biotech, SE) or vectors containing the tac promoter such as pKK223-3 (Pharmacia Biotech) or PMAL (New England Biolabs, MA, USA).

Moreover, the DNA binding protein gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes codino for the a- or α-factor or a promoter derived from a gene encoding a glycolytic enzyme such as the promoter of the enolase, glyceraldehyde-3-phosphate dehydrogenase (GAPDH), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

DNA binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with DNA binding protein sequence, provided such promoters are compatible with the host cell systems.

Transcription of a DNA encoding DNA binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to DNA binding protein DNA, but is preferably located at a site 5' from the promoter.

Advantageously, a eukaryotic expression vector encoding a DNA binding protein according to the invention may comprise a locus control region (LCR). LCRs are capable of directing high-level integration site independent expression of transgenes integrated into host cell chromatin, which is of importance especially where the DNA binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding DNA binding protein.

An expression vector includes any vector capable of expressing DNA binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding DNA binding protein may be inserted into a vector suitable for expression of cDNAs in mammalian cells, e.g. a CMV enhancer-based vector such as pEVRF (Matthias, et al., (1989) NAR 17, 6418).

In a preferred embodiment, the DNA binding protein constructs of the invention are expressed in plant cells under the control of transcriptional regulatory sequences that are known to function in plants. The regulatory sequences selected will depend on the required temporal and spatial expression pattern of the DNA binding protein in the host plant. Many plant promoters have been characterized and would be suitable for use in conjunction with the invention. By way of illustration, some examples are provided below:

A large number of promoters are known in the art which direct expression in specific tissues and organs (e.g. roots, leaves, flowers) or in cell types (e.g. leaf epidermal cells, leaf mesophyll cells, root cortex cells). For example, the maize PEPC promoter from the phosphoenol carboxylase gene (Hudspeth & Grula Plant Mol. Bio. 12: 579–589 (1989)) is green tissue-specific; the trpA gene promoter is pith cell-specific (WO 93/07978 to Ciba-Geigy); the TA29 promoter is pollen-specific (Mariani et al. Nature 347: 737–741 (1990); Mariani et al. Nature 357: 384–387 (1992)).

Other promoters direct transcription under conditions of presence of light or absence or light or in a circadian manner. For example, the GS2 promoter described by Edwards and Coruzzi, Plant Cell 1: 241–248 (1989) is induced by light, whereas the AS1 promoter described by Tsai and Corzzi, EMBO J 9: 323–332 (1990) is expressed only in conditions of darkness.

Other promoters are wound-inducible and typically direct transcription not just on wound induction, but also at the sites of pathogen infection. Examples are described by Xu et al. (Plant Mol. Biol. 22: 573–588 (1993)); Logemann et al. (Plant Cell 1: 151–158 (1989)); and Firek et al. (Plant Mol Biol 22: 129–142 (1993)).

A number of constitutive promoters can be used in plants. These include the Cauliflower Mosaic Virus 35S promoter (U.S. Pat. Nos. 5,352,605 and 5,322,938, both to Monsanto) including minimal promoters (such as the −90 or −46 CaMV 35S promoter) linked to other regulatory sequences, the rice actin promoter (McElroy et al. Mol. Gen. Genet. 231: 150–160 (1991)), and the maize and sunflower ubiquitin promoters (Christensen et al. Plant Mol Biol. 12: 619–632 (1989); Binet et al. Plant Science 79: 87–94 (1991)).

Using promoters that direct transcription in the plant species of interest, the DNA binding protein of the invention can be expressed in the required cell or tissue types. For example, if it is the intention to utilize the DNA binding protein to regulate a gene in a specific cell or tissue type, then the appropriate promoter can be used to direct expression of the DNA binding protein construct.

An appropriate terminator of transcription is fused downstream of the selected DNA binding protein containing transgene and any of a number of available terminators can be used in conjunction with the invention. Examples of transcriptional terminator sequences that are known to function in plants include the nopaline synthase terminator found in the pBI vectors (Clontech catalog 1993/1994), the E9 terminator from the rbcS gene (ref), and the tm1 terminator from Cauliflower Mosaic Virus.

A number of sequences found within the transcriptional unit are known to enhance gene expression and these can be used within the context of the current invention. Such sequences include intron sequences which, particularly in monocotyledonous cells, are known to enhance expression. Both intron 1 of the maize Adh1 gene and the intron from the maize bronze1 gene have been found to be effective in enhancing expression in maize cells (Callis et al. Genes Develop. 1: 1183–1200 (1987)) and intron sequences are frequently incorporated into plant transformation vectors, typically within the non-translated leader.

A number of virus-derived non-translated leader sequences have been found to enhance expression, especially in dicotyledonous cells. Examples include the "106" leader sequence of Tobacco Mosaic Virus, and simlar leader sequences of Maize Chlorotic Mottle Virus and Alfalfa Mosaic Virus (Gallie et al. Nucl. Acids Res. 15: 8693–8711 (1987); Shuzeski et al. Plant Mol Biol 15: 65–79 (1990)).

The DNA binding proteins of the current invention are targeted to the cell nucleus so that they are able to interact with host cell DNA and bind to the appropriate DNA target in the nucleus and regulate transcription. To effect this, a Nuclear Localization Sequence (NLS) is incorporated in frame with the expressible zinc finger construct. The NLS can be fused either 5' or 3' to the zinc finger encoding sequence.

The NLS of the wild-type Simian Virus 40 Large T-Antigen (Kalderon et al. Cell 37: 801–813 (1984); Markland et al. Mol. Cell Biol. 7: 4255–4265 (1987)) is an appropriate NLS and has previously been shown to provide an effective nuclear localization mechanism in plants (van der Krol et al. Plant Cell 3: 667–675 (1991)). However, several alternative NLSs are known in the art and can be used instead of the SV40 NLS sequence. These include the Nuclear Localization Signals of TGA-1A and TGA-1B (van der Krol et al.; Plant Cell 3: 667–675 (1991)).

A variety of transformation vectors are available for plant transformation and the DNA binding protein encoding genes of the invention can be used in conjunction with any such vectors. The selection of vector will depend on the preferred transformation technique and the plant species which is to be transformed. For certain target species, different selectable markers may be preferred.

For Agrobacterium-mediated transformation, binary vectors or vectors carrying at least one T-DNA border sequence are suitable. A number of vectors are available including pBIN19 (Bevan. Nucl. Acids Res. 12: 8711–8721 (1984), the pBI series of vectors, and pCIB10 and derivatives thereof (Rothstein et al. Gene 53: 153–161 (1987); WO 95/33818 to Ciba-Geigy).

Binary vector constructs prepared for Agrobacterium transformation are introduced into an appropriate strain of *Agrobacterium tumefaciens* (for example, LBA 4044 or GV 3101) either by triparental mating (Bevan; Nucl. Acids Res. 12: 8711–8721 (1984)) or direct transformation (Höfgen & Willmitzer, Nucl. Acids Res. 16: 9877 (1988)).

For transformation which is not Agrobacterium-mediated (i.e. direct gene transfer), any vector is suitable and linear DNA containing only the construct of interest may be preferred. Direct gene transfer can be undertaken using a single DNA species or multiple DNA species (co-transformation; Schroder et al. Biotechnology 4: 1093–1096 (1986)).

Particularly useful for practising several embodiments of the present invention are expression vectors that provide for the transient expression of DNA encoding a DNA binding protein in plant cells or mammalian cells. Transient expression usually involves the use of an expression vector that is able to replicate efficiently in a host cell, such that the host cell accumulates many copies of the expression vector, and, in turn, synthesises high levels of DNA binding protein. For the purposes of the present invention, transient expression systems are useful e.g. for identifying DNA binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing DNA binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the DNA binding protein. Suitable prokaryotes include eubacteria, such as Gram-negative or Gram-positive organisms, such as *E. coli*, e.g. *E. coli* K-12 strains, DH5α and HB101, or Bacilli. Further hosts suitable for the DNA binding protein encoding vectors include eukaryotic microbes such as filamentous fungi or yeast, e.g. *Saccharomyces cerevisiae*. Higher eukaryotic cells include plant cells and animal cells such as insect and vertebrate cells, particularly mammalian cells including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a multicellular host organism.

DNA may be stably incorporated into cells or may be transiently expressed using methods known in the art. Stably transfected cells may be prepared by transfecting cells with an expression vector having a selectable marker gene, and growing the transfected cells under conditions selective for cells expressing the marker gene. To prepare transient transfectants, cells are transfected with a reporter gene to monitor transfection efficiency.

To produce such stably or transiently transfected cells the cells should be transfected with a sufficient amount of the DNA binding protein-encoding nucleic acid to form the DNA binding protein. The precise amounts of DNA encoding the DNA binding protein may be empirically determined and optimised for a particular cell and assay.

Host cells are transfected or, preferably, transformed with the above-mentioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions whereby the DNA binding protein encoded by the DNA is expressed. The composition of suitable media is known to those in the art, so that they can be readily prepared. Suitable culturing media are also commercially available.

Transformation of plant cells is normally undertaken with a selectable marker which may provide resistance to an antibiotic or to a herbicide. Selectable markers that are routinely used in transformation include the nptII gene which confers resistance to kanamycin (Messing & Vierra Gene 19: 259–268 (1982); Bevan et al. Nature 304: 184–187 (1983)), the bar gene which confers resistance to the herbicide phosphinothricin (White et al. Nucl. Acids Res. 18: 1062(1990); Spencer et al. Theor. Appl. Genet. 79: 625–631 (1990)), the hph gene which confers resistance to the antibiotic hygromycin (Blochlinger & Diggelmann Mol. Cell Biol. 4: 2929–2931 (1984)), and the dhfr gene which confers resistance to methotrexate (Bourouis et al. EMBO J 2: 1099–1104 (1983)). More recently, a number of selection systems have been developed which do not rely of selection for resistance to antibiotic or herbicide. These include the inducible isopentyl transferase system described by Kunkel et al. (Nature Biotechnology 17: 916–919 (1999).

Although specific protocols may vary from species to species, transformation techniques are well known in the art for most commercial plant species.

In the case of dicotyledonous species, Agrobacterium-mediated transformation is generally a preferred technique as it has broad application to many dicotyledons species and is generally very efficient. Agrobacterium-mediated transformation generally involves the co-cultivation of Agrobacterium with explants from the plant and follows procedures and protocols that are known in the art. Transformed tissue is generally regenerated on medium carrying the appropriate selectable marker. Protocols are known in the art for many dicotyledonous crops including (for example) cotton, tomato, canola and oilseed rape, poplar, potato, sunflower, tobacco and soybean (see for example EP 0 317 511, EP 0 249 432, WO 87/07299, U.S. Pat No. 5,795,855).

In addition to Agrobacterium-mediated transformation, various other techniques can be applied to dicotyledons. These include PEG and electroporation-mediated transformation of protoplasts, and microinjection (see for example Potrykus et al. Mol. Gen. Genet. 199: 169–177 (1985); Reich et al. Biotechnology 4: 1001–1004 (1986); Klein et al. Nature 327: 70–73 (1987)). As with Agrobacterium-mediated transformation, transformed tissue is generally regenerated on medium carrying the appropriate selectable marker using standard techniques known in the art.

Although Agrobacterium-mediated transformation has been applied successfully to monocotyledonous species such as rice and maize and protocols for these approaches are available in the art, the most widely used transformation techniques for monocotyledons remain particle bombardment, and PEG and electroporation-mediated transformation of protoplasts.

In the case of maize, Gordon-Kamm et al. (Plant Cell 2: 603–618 (1990)). Fromm et al. (Biotechnology 8: 833–839 (1990) and Koziel et al. (Biotechnology 11: 194–200 (1993)) have published techniques for transformation using particle bombardment.

In the case of rice, protoplast-mediated transformation for both Japonica- and Indica-types has been described (Zhang et al. Plant Cell Rep. 7: 379–384 (1988); Shimamoto et al. Nature 338: 274–277; Datta et al. Biotechnology 8: 736–740 (1990)) and both types are also routinely transformable using particle bombardment (Christou et al. Biotechnology 9: 957–962 (1991)).

In the case of wheat, transformation by particle bombardment has been described for both type C long-term regenerable callus (Vasil et al. Biotechnology 10: 667–674 (1992)) and immature embryos and immature embryo-derived callus (Vasil et al. Biotechnology 11: 1553–1558 (1993); Weeks et al. Plant Physiol. 102: 1077–1084 (1993)). A further technique is described in published patent applications WO 94/13822 and WO 95/33818.

The DNA binding protein constructs of the invention are suitable for expression in a variety of different organisms. However, to enhance the efficiency of expression it may be necessary to modify the nucleotide sequence encoding the DNA binding protein to account for different frequencies of codon usage in different host organisms. Hence it is preferable that the sequences to be introduced into organisms, such as plants, conform to preferred usage of codons in the host organism.

In general, high expression in plants is best achieved from codon sequences that have a GC content of at least 35% and preferably more than 45%. This is thought to be because the existence of ATTTA motifs destabilize messenger RNAs and the existence of AATAAA motifs may cause inappropriate polyadenylation, resulting in truncation of transcription. Murray et al. (Nucl. Acids Res. 17: 477–498 (1989)) have shown that even within plants, monocotyledonous and dicotyledonous species have differing preferences for codon usage, with monocotyledonous species generally preferring GC richer sequences. Thus, in order to achieve optimal high level expression in plants, gene sequences can be altered to accommodate such preferences in codon usage in such a manner that the codons encoded by the DNA are not changed.

Plants also have a preference for certain nucleotides adjacent to the ATG encoding the initiating methionine and for most efficient translation, these nucleotides may be modified. To facilitate translation in plant cells, it is preferable to insert, immediately upstream of the ATG representing the initiating methionine of the gene to be expressed, a "plant translational initiation context sequence". A variety of sequences can be inserted at this position. These include the sequence the sequence 5'-AAGGAGATATAACAATG-3' (SEQ ID NO:11) (Prasher et al. Gene 111: 229–233 (1992); Chalfie et al. Science 263: 802–805 (1992)), the sequence 5'-GTCGACCATG-3' (SEQ ID NO:12) (Clontech 1993/1994 catalog, page 210), and the sequence 5'-TAAACAATG-3' (Joshi et al. Nuci. Acids Res. 15: 6643–6653 (1987)). For any particular plant species, a survey of natural sequences available in any databank (e.g. GenBank) can be undertaken to determine preferred "plant translational initiation context sequences" on a species-by-species basis.

Any changes that are made to the coding sequence can be made using techniques that are well known in the art and include site directed mutagenesis, PCR, and synthetic gene construction. Such methods are described in published patent applications EP 0 385 962 (to Monsanto), EP 0 359 472 (to Lubrizol) and WO 93/07278 (to Ciba-Geigy). Well known protocols for transient expression in plants can be used to check the expression of modified genes before their transfer to plants by transformation.

C. DNA Binding Ligands

A DNA binding ligand according to the invention is typically any molecule capable of binding DNA. A variety of DNA binding ligands are known in the art and include acridine orange, 9-Amino-6-chloro-2-methoxyacridine, actinomycin D, 7-aminoactinomycin D, echinomycin, dihydroethidium, ethidium-acridine heterodimer, ethidium bromide, propidium iodide, hexidium iodide, Hoechst 33258, Hoechst 33342, hydroxystibamidine, psoralen, Distamycin A, calicheamicin oligosaccharides, triple-helix forming oligos or PNA, pyrole-imidazole polyamides and peptides or peptide derivatives. These peptides or peptide derivatives are small synthetic polypeptides that can be taken up by plant or animal cells and bind DNA. These polypeptides bind with low affinity to DNA in the absence of a DNA binding molecule but their interaction with DNA may be strengthened by binding of a DNA binding molecule to the target DNA molecule. Such peptide or peptide derivatives have been demonstrated to bind DNA and may be selected from a synthetic library of peptides containing unnatural amino acids as described by Lescrinier et al., Chem. Eur. J. 4:425–433 (1998). Also included within the meaning of the term DNA binding ligand and DNA binding molecules are molecules capable of binding RNA and/or other nucleic acids.

Derivatives of DNA binding ligands are also included provided that they are capable of binding DNA, RNA and/or other nucleic acids.

In a preferred embodiment, a DNA binding ligand according to the invention is capable of modulating the topology, locally or otherwise, of the nucleic acid to which it is bound. In particular, a DNA binding ligand according to the invention may be capable of modulating the topology of a juxtaposed nucleic acid sequence motif to which it is desired to bind a DNA binding molecule according to the invention.

Preferred DNA binding ligands have shape and charge characteristics that allow them to reside along the DNA, in either the minor or major groove, intercalate or a combination of these.

Suitable DNA binding ligands in addition to those known in the art may be selected by the use of nucleic acid binding assays. For example, a candidate DNA binding ligand, preferably a plurality of candidate DNA binding ligands, is contacted with nucleic acid and binding determined. The nucleic acids may for example be labelled with a detectable label, such as a fluorophore/fluorochrome, such that after a wash step binding can be determined easily, for example by monitoring fluorescence. The nucleic acid with which the candidate binding ligands are contacted may be non-specific nucleic acids, such as a random oligonucleotide library or sonicated genomic DNA and the like. Alternatively, a specific sequence may be used or partially randomised library of sequences.

It is particularly preferred that DNA binding ligands of the invention bind to DNA in a sequence and/or topology dependent manner so that binding can be restricted to a particular target DNA thus enhancing the specificity of the gene switch. Specificity of binding may be determined, for example, by comparing the binding of the DNA binding ligand to a target sequence with binding to a mixture of non-specific DNA molecules.

DNA binding ligands according to the invention may bind conditionally to nucleic acid. For example, psoralen is a ligand that can bind DNA covalently if illuminated at wavelengths of about 400 nm or less. Ligands capable of binding nucleic acids in more than one manner may be employed in the current invention. Such ligands may bind or associate with the DNA via any one or more mechanism(s) as outlined above.

In a preferred embodiment, libraries of DNA binding ligands may be prepared. In particular, libraries of DNA binding ligands may be immobilised to a solid phase, such as a substantially planar solid phase, including membranes and non-porous substrates such as plastic and glass. The resulting immobilised library may conveniently be used in high throughput screening procedures.

In another preferred embodiment, libraries of synthetic peptides may be prepared. These may be immobilised on a solid phase, such as a bead, and may have weak affinity for DNA. In high throughput screens, DNA target (either specific or a random oligonucleotide) may be labeled with a fluorescent label and the DNA binding molecule may be labeled with an antibody having a different fluorescent label. Interaction of the DNA ligand with DNA may be enhanced in the presence of the DNA binding molecule and the three molecules may be selected by monitoring the fluorescence of the two labels on the solid support.

Particularly preferred DNA binding ligands are those which are substantially non toxic to plants and or animal cells such that they may be administered to said cells and modulate binding of the DNA binding molecule without having an adverse effect on the cells. Thus it may be desirable to pre-screen compounds to exclude toxic compounds.

Furthermore, given that DNA binding ligands should typically be capable of being taken up by the cells of animals or plants, preferred compounds are suitable for administration to animals and plants. For example, preferred compounds are capable of being taken up via the leaves (for foliar application) or roots of plants (for application to the soil) or of permeating seeds (for use in seed treatment). It may also preferred to use compounds that can be taken up by bacteria, yeast and/or fungi that can themselves be delivered to the target host organism. The compounds should also preferably be stable in the soil and/or plant for prolonged periods. In the case of animals, preferred compounds are suitable for topical or oral adminstration.

D. Target DNA

The term 'target DNA' refers to any DNA for use in the methods of the invention. This DNA may be of known sequence, or may be of unknown sequence. This DNA may be prepared artificially in a laboratory, or may be a naturally occurring DNA. This DNA may be in substantially pure form, or may be in a partially purified form, or may be part of an unpurified or heterogeneous sample. Preferably, the target DNA is a putative promoter or other transcription regulatory region such as an enhancer. More preferably, the target DNA is in substantially pure form. Even more preferably, the target DNA is of known sequence. In a most preferred embodiment, the target DNA is purified DNA of known sequence of a promoter from a gene of interest, for example from a gene suspected of being associated with a disease state, more preferably from a gene useful in gene therapy.

Examples of target sequences of interest include sequence motifs that are bound by transcription factors, such as zinc fingers. Particular examples include the promoters of genes involved in the biosynthesis and catabolism of gibberellins (Phillips et al., Plant Physiol 108: 1049–1057 (1995), MacMillin et al., Plant Physiol 113: 1369–1377 (1997), Williams et al., Plant Physiol 117: 559–563 (1998); Thomas et al., PNAS 96: 4698–4703 (1999)); the promoters of genes whose products are reponsible for ripening (such as polygalacturonase and ACC oxidase; the promoters of genes involved in the biosythesis of volatile ester, which are important flavour compounds in fruits and vegetables (Dudavera et al., Plant Cell 8: 1137–1148 (1996): Dudavera et al., Plant J. 14: 297–304 (1998); Ross et al., Arch. Biochem. Biophys. 367: 9–16 (1999)); the promoters of genes involved in the biosynthesis of pharmaceutically important compounds; and the promoters of genes encoding allergens such as the peatnut allergens Arah1, Arah2 and Arah3 (Rabjohn et al., J. Clin. Invest 103: 535–542).

Other plant promoters of interest are the bronze promoter (Ralston et al., Genetics 119: 185–197 (1988) and Genbank Accession No. X07937.1) that directs expression of UDP-glucose flavanoid glycosyl-transferase in maize, the patatin-1 gene promoter (Jefferson et al., Plant Mo. Biol. 14: 995–1006 (1990)) that contains sequences capable of directing tuber-specific expression, and the phenylalanine ammonia lyase promoter (Bevan et al., Embo J. 8: 1899–1906 (1989)) though to be involved in responses to mechanical wounding and normal development of the xylem and flower.

Target DNA may also be provided as a plurality of sequences, for example where one or more residues in the nucleic acid sequence are varied or random. Examples of a plurality of sequences are libraries of nucleic acid sequences comprising putative zinc finger binding sites. Other sequence motifs that bind the DNA binding domain of a transcription factor may also be included in the plurality of sequences, typically varied or randomised at one or more positions. For example the chemically inducible promoter fragments described above may be randomised to produce a plurality of target DNA sequences for use in the screening methods of the present invention.

E. Assays

The methods of the present invention typically involve using a tripartite configuration of one or more DNA binding molecules, one or more DNA binding ligands and one or more target DNA sequences as described above to screen for (i) DNA binding molecules that bind to a target DNA in a manner that is modulatable by a DNA binding ligand (ii) DNA binding ligands that modulate binding of a DNA binding molecule to a target DNA and/or (iii) a target DNA that is bound modulatably by a DNA binding molecule as a result of an interaction with a DNA binding ligand. In other words the methods of the invention may be used to screen for any or all of the components of the gene switch system of the present invention.

Typically, one or two of the components is a known constant while two or one, respectively, of the other components are screened. For example, a given DNA binding molecule and target DNA may be used to screen a plurality of DNA binding ligands or candidate DNA binding ligands. Alternatively, a plurality of DNA binding molecules and of DNA binding ligands may be screened against a given target DNA. Other combinations are also envisaged.

Each component may be one individual molecular species or a plurality of molecular species. Where a plurality of species is used, they may be substantially all known, partially randomised or fully randomised. For example, the plurality of DNA binding molecules may be a randomised zinc finger library and the plurality of target DNA may be a library of nucleic acid molecules randomised at one or more, typically three or more contiguous, residues.

However, all three components may be screened for simultaneously. Thus, in a preferred embodiment, the invention provides a method for isolating multiple DNA binding molecules in the presence of multiple DNA binding ligands, said DNA binding molecules being selected using multiple target nucleic acid sequences in a single selection (isolation) procedure.

The library of candidate DNA binding molecules is preferably a phage display library, individual candidate molecules of the library optionally being structurally related to zinc finger transcription factors (for example see Choo and Klug, (1994) PNAS (USA) 91:11163–67, which describes aspects of such libraries and is incorporated herein by reference). This library is preferably constructed with DNA sequences of the form GCGNNNGCG (where all 64 middle triplets are represented in the mixture).

One or more DNA binding ligands means at least one DNA binding ligand, preferably two, three or four DNA binding ligands, more preferably five, six, or seven DNA binding ligands, most preferably a mixture of eight DNA binding ligands, or even more. The ligands may be in any molar ratio to one another within the mixture, but will preferably be approximately equimolar with one another.

Said method would preferably be carried out over at least 3, 4, 5 or 6 rounds of selection, preferably about 6 rounds of selection.

DNA binding molecules (such as phage clones) isolated by the above methods would preferably be individually assayed (for example in microtitre plates as described below) for binding to the target DNA (such as a GCGNNNGCG mixture) in the presence and absence of a mixture of the DNA binding ligands to identify clones which are capable of ligand-modulatable binding.

Those phage clones which are capable of ligand-modulatable binding would preferably be tested in the presence of a mixture of the eight ligands, in order to deduce the optimum target DNA sequence, for example using different or variant target DNA sequences, or by the binding site signature method method (see Choo and Klug, (1994) PNAS (USA) 91:11163–67).

Where candidate DNA binding molecules are used rather than molecules known or determined to have DNA binding properties, the method of the invention would preferably feature a pre-selection step to remove candidate DNA binding molecules which do not require ligand to bind the DNA.

Association of the candidate DNA binding molecule with the target DNA may be assessed by any suitable means known to those skilled in the art. For example, the DNA may be immobilised by biotinylation and linking to beads such as streptavidin coated beads (Dynal). In a preferred embodiment wherein the DNA binding molecules are phage displayed polypeptides, binding of said molecules to the DNA may be assessed by eluting those phage which bind, and infecting logarithmic phase *E. coli* TG1 cells. The presence of infective particles eluted from the DNA indicates that association of the DNA binding molecule(s) with the DNA has occurred. Alternatively, association of the candidate DNA binding molecule(s) with the target DNA may be assessed by Scintillation Proximity Assay (SPA). For example, the target DNA could be biotinylated and immobilised to streptavidin coated SPA beads, and the candidate DNA binding molecules may be radioactively labelled, for example with $^{35}$S-Methionine where the molecules are polypeptides. Association of the candidate DNA binding molecules with the target DNA could then be assessed by monitoring the readout of the SPA. Alternatively, the association could be monitored by fluorescent resonance energy transfer (FRET). In this case, the target DNA could be labelled with a donor fluor, and the DNA binding molecule(s) could be labelled with asuitable acceptor fluor. Whilst the two entities are seperated, no FRET would be observed, but if association (binding) took place, then there would be a change in the amount of FRET observed, this allowing assessment of the degree of associaiton.

Association of the candidate DNA binding molecule with the target DNA may also be assessed by bandshift assays. Bandshift assays are conducted by measuring the mobility of one or more of the components of the assay, for example the mobility of the DNA, as it is electrophoresed through a suitable gel such as a polyacrylamide acrylamide gel, as is well known to those skilled in the art. In order to assess the association of the candidate DNA binding molecule with the target DNA, the mobility of the DNA could be measured in the presence and absence of the candidate DNA binding molecule. If the mobility of the target DNA is essentially the same in the presence or absence of the candidate DNA binding molecule, then it may be inferred that the molecules do not associate, or that the association is weak. If the mobility of the DNA is retarded in the presence of the candidate DNA binding molecule, then it may be inferred that the candidate molecule is associating with or binding to the DNA.

Association of the candidate DNA binding molecule with the target DNA may also be assessed using filter binding assays. For example, the target DNA molecule may be immobilised on a suitable filter, such as a nitrocellulose filter. The candidate DNA binding molecule may then be labelled, for example radioactively labelled, and contacted with the immobilised target DNA. The binding of or association with the target DNA may be assessed by comparing the amount of labelled candidate DNA binding molecule which associates with the filter only to the amount of labelled candidate DNA binding molecule which associates with the filter-immobilised target DNA. If more labelled candidate DNA binding molecule associates with the immobilised DNA than with the filter only, it may be inferred that the target DNA molecule does indeed associate with the candidate binding molecule.

Binding affinities may be estimated by any suitable means known to those skilled in the art. Binding affinities for the purposes of this invention may be absolute or may be relative. Binding affinities may be determined biochemically, or may simply be estimated by assessing the association of the candidate DNA binding molecule with the target DNA as described above. As used herein, the term binding affinity may refer to a simple estimation of the association of one component of the system with another.

Another suitable detection method is the use of target DNA sequences linked to reporter constructs, such as bacterial luciferase or lacZ. Preferably, the reporter gene product can be measured using optical detection techniques. By way of example, a multiarray format could be used with a different candidate ligand in each position in the array (such as a microtitre plate well) and the same library of zinc finger proteins and target DNA sequences at each position. The zinc finger proteins will generally be fused to a transcriptional activation domain such as the GAL4 acidic activation domain. Transcription may then be compared in the various wells and wells showing a variation in transcription compared to a control well with no ligand may be selected and the ligand further tested to identify specific target sequences/zinc finger proteins whose interaction is affected. These further tests may again be performed using an array format in which this time the DNA binding ligand is kept constant and the target sequence/zinc fingers varied. Phage display techniques as described above may be used to simplify the isolation of suitable zinc finger proteins. Although described in the context of zinc fingers, this method could be applied to other DNA binding molecules.

It is envisaged that the methods of the invention may be applied in vivo, for example they could be applied to the selection or isolation of DNA binding molecules capable of associating with target DNA in vivo inside one or more cells, in a manner analagous to the one-hybrid system.

It is envisaged that the methods of the invention may be practised in parallel. For example, multiple target DNAs could be used in a single selective step, thereby enabling multiple DNA binding molecules to be isolated simultaneously, even in the same physical vessel. Said multiple DNA binding molecules may preferably be different from one another. Said multiple DNA binding molecules may have similar or identical DNA binding specificities, or may preferably have different DNA binding specificities.

The invention may be worked using multiple DNA binding ligands, either separately or in combination. For example, a target nucleic acid sequence may be used to isolate DNA binding molecules according to the methods essentially as disclosed above, with the modification that more than one DNA binding ligand may be present. In this way, it is possible to isolate multiple DNA binding molecules which require different ligands to bind to the same target nucleic acid sequence(s).

By way of example, a particular embodiment of the method of the invention is as follows:

1. Bacterial colonies containing phage libraries that express a library of zinc fingers randomised at one or more DNA binding residues (see section A.) are transferred from plates to culture medium. Bacterial cultures are grown overnight at 30° C. Culture supernatant containing phages is obtained by centrifugation.

2. 10 pmol of biotinylated target DNA immobilised on 50 mg streptavidin beads (Dynal) is incubated with 1 ml of the bacterial culture supernatant diluted 1:1 with PBS containing 50 µM $ZnCl_2$, 4% Marvel, 2% Tween for 1 hour at 20° C. on a rolling platform as a preselection step to remove phage that bind to the target DNA in the absence of a ligand.

3. After this time, 0.5 ml of phage solution is transferred to a streptavidin coated tube and incubated with biotinylated DNA target site in the presence of a candidate DNA binding ligand and 4 µg poly [d(I-C)]. After a one hour incubation the tubes are washed 20 times with PBS containing 50 µM $ZnCl_2$ and 1% Tween, and 3 times with PBS containing 50 µM $ZnCl_2$ to remove non-binding phage.

4. The remaining phage are eluted using 0.1 ml 0.1 M triethylamine and the solution is neutralised with an equal volume of 1 M Tris-Cl (pH 7.4).

5. Logarithmic-phase *E. coli* TG1 cells are infected with eluted phage, and grown overnight, as described above, to prepare phage supernatants for subsequent rounds of selection.

6. After 4 rounds of selection (steps 1 to 5), bacteria are plated and phage prepared from 96 colonies are screened for binding to the DNA target site in the presence and absence of the ligand. Binding reactions are carried out in wells of a streptavidin-coated microtitre plate (Boehringer Mannheim) and contain 50 µl of phage solution (bacterial culture supernatant diluted 1:1 with PBS containing 50 µM $ZnCl_2$, 4% Marvel, 2% Tween), 0.15 pmol DNA target site and 0.25 µg poly [d(I-C)]. When added, the DNA binding ligand is present at a concentration of about 1 µM.

7. After a one hour incubation the wells are washed 20 times with PBS containing 50 µM $ZnCl_2$ and 1% Tween (and also ligand at a concentration of 1 µM where appropriate), and 3 times with PBS containing 50 µM $ZnCl_2$.

8. Bound phage are detected by ELISA (carried out in the presence of the ligand at a concentration of about 1 µM where appropriate) with horseradish peroxidase-conjugated anti-M13 IgG (Pharmacia Biotech) and quantitated using SOFTMAX 2.32 (Molecular Devices).

9. Single colonies of transformants obtained after four rounds of selection as described, are grown overnight in culture. Single-stranded DNA is prepared from phage in the culture supernatant and sequenced using the Sequenase™ 2.0 kit (U.S. Biochemical Corp.). The amino acid sequences of the zinc finger clones are deduced.

In the above example, only one target DNA sequence was used. Where a library of DNA sequences is used, the library of sequences can be screened using the ligand and selected phage expressing the zinc finger of interest to identify specific target DNA sequences. This may conveniently be carried out with the DNA sequences arrayed onto a solid substrate.

In the above example, the zinc fingers (DNA binding molecules) are present on phage. However, alternative methods for displaying the DNA molecules could be used. As descibed in section A above, an entirely in vitro polysome display system has also been reported (Mattheakis et al., (1994) Proc Natl Acad Sci USA, 91, 9022–6) in which nascent peptides are physically attached via the ribosome to the RNA which encodes them. Using a library of RNA/ribosomes expressing the DNA binding molecules, screening is performed in a similar manner to the phage display method except that typically, after an initial preselection step to remove DNA binding molecules that bind in the absence of the ligand only one selection step is performed and the resulting DNA binding molecules identified by cloning the RNA from the RNA/ribosome complexes and sequencing the clones obtained.

To assist in isolating and/or identifying complexes comprising a target DNA, a DNA binding molecule and a DNA binding ligand, it may be desirable to label one or more of the components with a detectable label. For example, the DNA may be labelled with a fluorescent tag and the DNA binding molecule labelled with biotin, such that an enzyme conjugate such as horse radish peroxidase (HRP), that catalyses an optically detectable change in a substrate (different from the fluorescent tag) can be used. If the DNA binding ligand is attached to a bead, then tripartite complexes can be detected because they will both fluoresce and give HRP activity.

A further method which is useful where multiple candidate DNA binding ligands are to be screened involves the use of beads to which are attached different peptide tags. Known combinatorial chemistry techniques are used to produce a library of beads whereby the peptide tag can be used to identify unambiguously the ligand attached to the same bead. Complexes comprising the ligand, a target DNA and a DNA binding molecule can be identified by the use of labelled target DNA and DNA binding molecules as described above. Beads comprising a tripartite complex can then be selected and the identity of the tag determined by spectroscopy techniques which will then give the identity of the ligand.

In general, a bead format is advantageous since it allows easier isolation of productive tripartite complexes and pre-screening.

In a further aspect of the invention, DNA binding molecules according to the invention may be advantageously used to determine the sequence composition of a sample of target DNA. For example, a DNA binding molecule according to the invention may be prepared which binds to a known target DNA sequence. By applying this molecule to, or contacting it with, one or more test DNA samples and monitoring its binding thereto, it is possible to determine whether said DNA sample(s) contain the cognate DNA recognition site of the DNA binding molecule, and therefore derive information about the nucleotide composition of said DNA test sample(s). Such analyses may be advantageously conducted using the binding site signature method (see Choo and Klug, (1994) PNAS (USA) 91:11163–67).

Individual phage clones could advantageously be assayed for binding of their cognate DNA sequence(s) in the presence or absence of individual ligands, to monitor which particular ligand modulates binding.

Clearly, it may be that more than one ligand modulates binding of DNA binding molecules to their cognate DNA sequence(s). Preferably, individual DNA binding molecules (ie. phage clones) may be assayed for binding to target DNA sequence(s) in the presence of discrete ligand mixtures, wherein each ligand mixture preferably contains a unique mixture of ligands. In this way, the particular ligands which may modulate binding of a particular DNA binding molecule to its cognate target DNA sequence may advantageously be determined. For example, if it is found that two mixtures—one lacking ligand X and the other lacking ligand Y—are incapable of inducing binding, then a mixture of ligands X and Y may have the effect of moduating the binding. This could advantageously be further investigated according to the methods of the invention as described herein.

It is envisaged that this invention may be advantageously used in the isolation of a DNA binding ligand that is capable of modulating the association of a particular DNA binding molecule with its target DNA sequence. Accordingly, the invention provides a method for isolating one or more DNA binding ligands, said ligands each binding one or more target DNA sequence(s), wherein said binding to one or more target DNA sequence(s) modulates the binding of one or more DNA binding molecules, and wherein said DNA binding molecule(s) and said DNA binding ligands are different, said method comprising:

a) providing one or more target DNA molecule(s);

b) contacting the target DNA molecule(s) with one or more DNA binding molecule(s)

c) providing a library of candidate DNA binding ligands;

d) assessing the ability of candidate DNA binding ligands to modulate the association of the DNA binding molecule(s) with the target DNA molecule(s); and e) isolating those candidate DNA binding ligands which modulate the association of the DNA binding molecule(s) with the target DNA molecule(s).

In order to remove DNA binding molecules (for example phage displayed polypeptides) which bind DNA in a ligand-independent manner from a library, a pre-selection step may optionally be performed in the absence of ligand prior to each round of selection. This step removes from the library those clones which do not require ligand for DNA binding. Optionally, candidate molecules selected in this manner may be screened by ELISA for binding to the DNA target in the presence or absence of the ligand(s).

In the above described methods, in order to remove DNA binding molecules (for example phage displayed polypeptides) which bind DNA in a ligand-dependent manner from a library a pre-selection step may optionally be performed in the presence of ligand prior to each round of selection. This step removes from the library those clones which require ligand for DNA binding. Optionally, candidate molecules selected in this manner may be screened by ELISA for binding to the DNA target in the presence or absence of the ligand(s).

It is envisaged that the methods of the current invention may be advantageously applied to the selection of molecules capable of binding nucleic acids other than DNA, for example RNA. Structural considerations of RNA binding molecules are discussed in Afshar et al (Afshar et al, 1999: Curr. Op. Biotech. vol 10 pages 59–63). In particular, ligands suitable for use in the methods of the invention as applied to RNA include those ligands described above, or may be selected from aminoglycosides and their derivatives such as paromomycin, neomycin (for examples see Park et al., 1996: J. Am. Chem. Soc. vol 118 pp10150–10155); aminoglycoside mimetics (Tok and Rando 1998: J. Am. Soc. Chem. vol 120 pp 8279–8280); acridine derivatives (for examples see Hamy et al, 1998: Biochemistry vol 37 pp5086–5095); small peptides ('aptamers'); polycationic compounds (for examples see Wang et al, 1998: Tetrahedron 54 pp7955–7976) or any other nucleic acid binding molecules known to those skilled in the art. In a preferred embodiment, derivatives or libraries of said nucleic acid binding ligands may be prepared.

Accordingly, the present invention provides a method for isolating an RNA binding molecule which binds to a target RNA molecule in a manner modulatable by a RNA-binding ligand, wherein said RNA-binding ligand and said RNA-binding molecule are different, said method comprising; providing a target RNA molecule;

(a) contacting the target RNA molecule with a RNA-binding ligand, to produce a RNA-ligand complex;

(b) assessing the ability of candidate RNA-binding molecules to bind the target RNA molecule and the RNA-ligand complex; and isolating those candidate RNA-binding molecules which bind the target RNA molecule and RNA-ligand complex with different binding affinities.

It is further envisaged that the methods of the invention may be advantageously used to select nucleic acid sequences which allow binding of a particular DNA binding ligand/DNA binding molecule combination. For example, one may wish to isolate particular DNA sequences to which a given DNA binding molecule is able to bind, or to isolate only those DNA sequences which depend on the presence of ligand for the DNA binding molecule to associate with them.

Accordingly, there is provided a method for isolating target DNA sequences to which a particular DNA binding molecule will bind, said method comprising a) providing a library of target nucleic acid molecule(s);

b) contacting said nucleic acid molecules with a DNA binding molecule in the presence or absence of DNA binding ligand c) assessing the ability of the candidate target DNA molecule(s) to bind the DNA binding molecule; and d) isolating those target nucleic acid molecules which bind the DNA binding molecule.

A library of target nucleic acid molecule(s) according to the invention may preferably comprise a plurality of different nucleic acid molecules; preferably said nucleic acid molecules may be related to one another in terms of sequence homology.

A library of candidate nucleic acid binding molecule(s) according to the invention may preferably comprise a plurality of different candidate nucleic acid binding polypeptides; preferably said candidate nucleic acid binding polypeptides may be related to one another in terms of amino acid sequence homology.

It is envisaged that this method could be advantageously used in order to isolate DNA sequences which require ligand to associate with a known DNA binding molecule. For example, there may be a DNA sequence which is bound by a known DNA binding molecule in a ligand-independent manner, and it may be desirable to find a DNA sequence(s) which can also associate with the same wild-type DNA binding molecule, but which do so in a ligand-modulatable manner. Preferably, this may be accomplished according to the above method of the present invention.

F. Uses

The assay methods of the invention may be used to identify DNA binding molecules, DNA binding ligands and/or target DNA where the binding the DNA binding molecule to the target DNA is modulatable by the DNA binding ligand.

These components, such as DNA binding proteins according to the invention and identified by the assay methods of the invention, may be used individually or in combination in a wide variety of applications.

Thus, DNA binding proteins according to the invention and identified by the assay methods of the invention may be employed in a wide variety of applications, including diagnostics and as research tools. Advantageously, they may be employed as diagnostic tools for identifying the presence of particular nucleic acid molecules in a complex mixture. DNA binding molecules according to the invention can preferably differentiate between different target DNA molecules, and their binding affinities for the DNA target sequences are preferably modulated by DNA binding ligand(s). DNA binding molecules according to the invention are useful in switching or modulating gene expression, especially in gene therapy applications and agricultural biotechnology applications as described below.

Specifically, targeted DNA binding molecules, such as zinc fingers, according to the invention may moreover be employed in the regulation of gene transcription, for example by specific cleavage of nucleic acid sequences using a fusion polypeptide comprising a zinc finger targeting domain and a DNA cleavage domain, or by fusion of an transcriptional effector domain to a zinc finger, to activate or repress transcription from a gene which possesses the zinc finger binding sequence in its upstream sequences. Preferably, activation or repression only occurs in the presence of the DNA binding ligand since in a preferred embodiment the zinc fingers will not bind their target nucleic acid sequences in the absence of the ligand. Alternatively, activation only occurs in the absence of the DNA binding ligand, since the zinc fingers may not bind their target nucleic acid sequences in the presence of the ligand. Zinc fingers capable of differentiating between U and T may be used to preferentially target RNA or DNA, as required. Where RNA-targeting polypeptides are intended, these are included in the term "DNA binding molecule".

Thus DNA binding molecules according to the invention will typically require the presence of a transcriptional effector domain, such as an activation domain or a repressor domain. Examples of transcriptional activation domains include the VP16 and VP64 transactivation domains of Herpes Simplex Virus. Alternative transactivation domains are various and include the maize C1 transactivation domain sequence (Sainz et al., 1997, Mol. Cell. Biol. 17: 115–22) and P1 (Goffet al., 1992, Genes Dev. 6: 864–75; Estruch et al., 1994, Nucleic Acids Res. 22: 3983–89) and a number of other domains that have been reported from plants (see Estruch et al., 1994, ibid).

Instead of incorporating a transactivator of gene expression, a repressor of gene expression can be fused to the DNA binding protein and used to down regulate the expression of a gene contiguous or incorporating the DNA binding protein target sequence. Such repressors are known in the art and include, for example, the KRAB-A domain (Moosmann et al., Biol. Chem. 378: 669–677 (1997)) the engrailed domain (Han et al., Embo J. 12: 2723–2733 (1993)) and the snag domain (Grimes et al., Mol Cell. Biol. 16: 6263–6272 (1996)). These can be used alone or in combination to down-regulate gene expression.

Another possible application is the use of zinc fingers fused to nucleic acid cleavage moieties, such as the catalytic domain of a restriction enzyme, to produce a restriction enzyme capable of cleaving only target DNA of a specific sequence (see Kim et al., (1996) Proc. Natl. Acad. Sci. USA 93:1156–1160). Using such approaches, different DNA binding domains can be used to create restriction enzymes with any desired recognition nucleotide sequence, but which cleave DNA conditionally dependent on the presence or absence of a particular DNA binding ligand, for instance Distamycin A. It may also be possible to use enzymes other than those that cleave nucleic acids for a variety of purposes.

In a preferred embodiment, the zinc finger polypeptides of the invention may be employed to detect the presence of a particular target nucleic acid sequence in a sample.

Accordingly, the invention provides a method for determining the presence of a target nucleic acid molecule, comprising the steps of:

a) preparing a DNA binding protein by the method set forth above which is specific for the target nucleic acid molecule;

b) exposing a test system which may comprise the target nucleic acid molecule to the DNA binding protein under conditions which promote binding, and removing any DNA binding protein which remains unbound;

c) detecting the presence of the DNA binding protein in the test system.

Regulation of Gene Expression in vivo

In a particularly preferred embodiment of the present invention, DNA binding molecules capable of binding to a target DNA in a manner modulatable by a DNA binding ligand are used to regulate expression from a gene in vivo.

The target gene may be endogenous to the genome of the cell or may be heterologous. However, in either case it will comprise a target DNA sequence, such as a target DNA sequence described above, to which a DNA binding molecule of the invention binds in a manner modulatable by a DNA binding ligand. Where the DNA binding molecule is a polypeptide, it may typically be expressed from a DNA construct present in the host cell comprising the target sequence. The DNA construct is preferably stably integrated into the genome of the host cell, but this is not essential.

Thus in the case of polypeptide DNA binding molecules, a host cell according to the invention comprises a target DNA sequence and a construct capable of directing expression of the DNA binding molecule in the cell.

Suitable constructs for expressing the DNA binding molecule are known in the art and are described in section B above. The coding sequence may be expressed constitutively or be regulated. Expression may be ubiquitous or tissue-specific. Suitable regulatory sequences are known in the art and are also described in section B above. Thus the DNA construct will comprise a nucleic acid sequence encoding a DNA binding molecule operably linked to a regulatory sequence capable of directing expression of the DNA binding molecule in a host cell.

It may also be desirable to use target DNA sequences that include operably linked neighbouring sequences that bind transcriptional regulatory proteins, such as transactivators. Preferably the transcriptional regulatory proteins are endogenous to the cell. If not, they typically will need to be introduced into the host cell using suitable nucleic acid constructs.

Techniques for introducing nucleic acid constructs into host cells are known in the art for both prokaryotic and eukaryotic cells, including yeast, fungi, plant and animal cells. Many of these techniques are mentioned below in the section on the production of transgenic organisms.

Regulation of expression of the gene of interest which comprises a second coding sequence operably linked to the target DNA sequence is typically achieved by administering to the cell a DNA binding ligand according to the invention. Typically, the DNA binding ligand is a molecule such as Distamycin A which may be administered exogenously to the cell and taken up by the cell whereupon it may contact the DNA binding molecule and modulate its binding to the target sequence. However polypeptide DNA binding ligands may also be introduced into the cell either directly or by introducing suitable nucleic acid vectors, including viruses.

The target DNA sequence and the DNA construct encoding the DNA binding molecule are preferably stably integrated into the genome of the host cell. Where the host cell is a single celled organism or part of a multicellular organism, the resulting organism may be termed transgenic. The target DNA may, in a preferred embodiment, be a naturally occurring sequence for which a corresponding DNA binding molecule and DNA binding ligand have been identified using the screening methods of the invention.

The term "multicellular organism" here denotes all multicellular plants, fungi and animals except humans, i.e. prokaryotes and unicellular eukaryotes are excluded specifically. The term also includes an individual organism in all stages of development, including embryonic and fetal stages. A "transgenic" multicellular organisms is any multicellular organism containing cells that bear genetic information received, directly or indirectly, by deliberate genetic manipulation at the subcellular level, such as by microinjection or infection with recombinant virus. Preferably, the organism is transgenic by virtue of comprising at least a heterologous nucleotide sequence encoding a DNA binding molecule or target DNA as herein defined.

"Transgenic" in the present context does not encompass classical crossbreeding or in vitro fertilization, but rather denotes organisms in which one or more cells receive a recombinant DNA molecule. Transgenic organisms obtained by subsequent classical crossbreeding or in vitro fertilization of one or more transgenic organisms are included within the scope of the term "transgenic".

The term "germline transgenic organism" refers to a transgenic organism in which the genetic information has been taken up and incorporated into a germline cell, therefore conferring the ability to transfer the information to offspring. If such offspring, in fact, possess some or all of that information, then they, too, are transgenic multicellular organisms within the scope of the present invention.

The information to be introduced into the organism is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

"Operably linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence: in eukaryotes, generally, such control sequences include promoters and a transcription termination sequence. The term "control sequences" is intended to include, at a minimum components whose presence can influence expression, and can also include additional components whose presence is advantageous, for example, leader sequences and fusion partner sequences.

Since the nucleic acid constructs are typically to be integrated into the host genome, it is important to include sequences that will permit expression of polypeptides in a particular genomic context. One possible approach would to use homologous recombination to replace all or part of the endogenous gene whose expression it is desired to regulate with equivalent sequences comprising a target DNA in its regulatory sequences. This should ensure that the gene is subject to the same transcriptional regulatory mechanisms as the endogenous gene with the exception of the target DNA sequence. Alternatively, homologous recombination may be used in a similar manner but with the regulatory sequences also replaced so that the gene is subject to a different form of regulation.

However, if the construct encoding either the DNA binding molecule or target DNA is placed randomly in the genome, it is possible that the chromatin in that region will be transcriptionally silent and in a condensed state. If this occurs, then the polypeptide will not be expressed—these are termed position-dependent effects. To overcome this problem, it may be desirable to include locus control regions (LCRs) that maintain the intervening chromatin in a transcriptionally competent open conformation. LCRs (also known as scaffold attachment regions (SARS) or matrix attachment regions (MARs)) are well known in the art—an example being the chicken lysozyme A element (Stief et al., 1989, Nature 341: 343), which can be positioned around an expressible gene of interest to effect an increase in overall expression of the gene and diminish position dependent effects upon incorporation into the organism's genome (Stief et al., 1989, supra). Another example is the CD2 gene LCR described by Lang et al., 1991, Nucl. Acid. Res. 19: 5851–5856.

Thus, a polynucleotide construct for use in the present invention, to introduce a nucleotide sequence encoding a DNA binding molecule into the genome of a multicellular organism, typically comprises a nucleotide sequence encoding the DNA binding molecule operably linked to a regulatory sequence capable of directing expression of the coding sequence. In addition the polynucleotide construct may comprise flanking sequences homologous to the host cell organism genome to aid in integration. An alternative approach would be to use viral vectors that are capable of integrating into the host genome, such as retroviruses.

Preferably, a nucleotide construct for use in the present invention further comprises flanking LCRs.

Construction of Transgenic Organisms Expressing DNA Binding Molecules

A transgenic organism of the invention is preferably a multicellular eukaryotic organism, such as an animal, a plant or a fungus. Animals include animals of the phyla cnidaria, ctenophora, platyhelminthes, nematoda, annelida, mollusca, chelicerata, uniramia, crustacea and chordata. Uniramians include the subphylum hexpoda that includes insects such as the winged insects. Chordates includes vertebrate groups such as mammals, birds, reptiles and amphibians. Particular examples of mammals include non-human primates, cats, dogs, ungulates such as cows, goats, pigs, sheep and horses and rodents such as mice, rats, gerbils and hamsters.

Plants include the seed-bearing plants angiosperms and conifers. Angiosperms include dicotyledons and monocotyledons. Examples of dicotyledonous plants include tobacco, (*Nicotiana plumbaginifolia* and *Nicotiana tabacum*), arabidopsis (*Arabidopsis thaliana*), *Brassica napus, Brassica nigra, Datura innoxia, Vicia narbonensis, Vicia faba*, pea (*Pisum sativum*), cauliflower, carnation and lentil (*Lens culinaris*). Examples of monocotyledonous plants include cereals such as wheat, barley, oats and maize.

Production of Transgenic Animals

Techniques for producing transgenic animals are well known in the art. A useful general textbook on this subject is Houdebine, Transgenic animals—Generation and Use (Harwood Academic, 1997)—an extensive review of the techniques used to generate transgenic animals from fish to mice and cows.

Advances in technologies for embryo micromanipulation now permit introduction of heterologous DNA into, for example, fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals. Those techniques as well known. See reviews of standard laboratory procedures for microinjection of heterologous DNAs into mammalian fertilized ova, including Hogan et al., Manipulating the Mouse Embryo, (Cold Spring Harbor Press 1986); Krimpenfort et al., Bio/Technology 9:844 (1991); Palmiter et al., Cell, 41: 343 (1985); Kraemer et al., Genetic manipulation of the Mammalian Embryo, (Cold Spring Harbor Laboratory Press 1985); Hammer et al., Nature, 315: 680 (1985); Wagner et al., U.S. Pat. No. 5,175,385; Krimpenfort et al., U.S. Pat. No. 5,175,384, the respective contents of which are incorporated herein by reference Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology as described in Schnieke, A. E. et al., 1997, Science, 278: 2130 and Cibelli, J. B. et al., 1998, Science, 280: 1256. Using this method, fibroblasts from donor animals are stably transfected with a plasmid incorporating the coding sequences for a binding domain or binding partner of interest under the control of regulatory. Stable transfectants are then fused to enucleated oocytes, cultured and transferred into female recipients.

Analysis of animals which may contain transgenic sequences would typically be performed by either PCR or Southern blot analysis following standard methods.

By way of a specific example for the construction of transgenic mammals, such as cows, nucleotide constructs comprising a sequence encoding a DNA binding molecule are microinjected using, for example, the technique described in U.S. Pat. No. 4,873,191, into oocytes which are obtained from ovaries freshly removed from the mammal. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000 g to visualize the pronuclei for injection and then cultured from the zygote to morula or blastocyst stage in oviduct tissue-conditioned medium. This medium is prepared by using luminal tissues scraped from oviducts and diluted in culture medium. The zygotes must be placed in the culture medium within two hours following microinjection.

Oestrous is then synchronized in the intended recipient mammals, such as cattle, by administering coprostanol. Oestrous is produced within two days and the embryos are transferred to the recipients 5–7 days after estrous. Successful transfer can be evaluated in the offspring by Southern blot.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example, in WO91/10741.

Production of Transgenic Plants

Techniques for producing transgenic plants are well known in the art. Typically, either whole plants, cells or protoplasts may be transformed with a suitable nucleic acid construct encoding a DNA binding molecule or target DNA (see above for examples of nucleic acid constructs). There are many methods for introducing transforming DNA constructs into cells, but not all are suitable for delivering DNA to plant cells. Suitable methods include Agrobacterium infection (see, among others, Turpen et al., 1993, J. Virol. Methods, 42: 227–239) or direct delivery of DNA such as, for example, by PEG-mediated transformation, by electroporation or by acceleration of DNA coated particles. Acceleration methods are generally preferred and include, for example, microprojectile bombardment. A typical protocol for producing transgenic plants (in particular moncotyledons), taken from U.S. Pat. No. 5,874,265, is described below.

An example of a method for delivering transforming DNA segments to plant cells is microprojectile bombardment. In this method, non-biological particles may be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming both dicotyledons and monocotyledons, is that neither the isolation of protoplasts nor the susceptibility to Agrobacterium infection is required. An illustrative embodiment of a method for delivering DNA into plant cells by acceleration is a Biolistics Particle Delivery System, which can be used to propel particles coated with DNA through a screen, such as a stainless steel or Nytex screen, onto a filter surface covered with plant cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and may be too large for attaining a high frequency of transformation. This may be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one may obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step may include assaying cultures directly for a screenable trait or by exposing the bombarded cultures to a selective agent or agents.

An example of a screenable marker trait is the red pigment produced under the control of the R-locus in maize. This pigment may be detected by culturing cells on a solid support containing nutrient media capable of supporting growth at this stage, incubating the cells at, e.g., 18° C. and greater than 180 $\mu$E m$^{-2}$ s$^{-1}$, and selecting cells from colonies (visible aggregates of cells) that are pigmented. These cells may be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g. for one to two weeks) and transferred to filters overlaying solid medium containing from 1–3 mg/l bialaphos. While ranges of 1–3 mg/l will typically be preferred, it is proposed that ranges of 0.1–50 mg/l will find utility in the practice of the invention. The type of filter for use in bombardment is not believed to be particularly crucial, and can comprise any solid, porous, inert support.

Cells that survive the exposure to the selective agent may be cultured in media that supports regeneration of plants. Tissue is maintained on a basic media with hormones for about 2–4 weeks, then transferred to media with no hormones. After 2–4 weeks, shoot development will signal the time to transfer to another media.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 $\mu$E $m^{-2}$ $s^{-1}$ of light. Plants are preferably matured either in a growth chamber or greenhouse. Regeneration will typically take about 3–12 weeks. During regeneration, cells are grown on solid media in tissue culture vessels. An illustrative embodiment of such a vessel is a petri dish. Regenerating plants are preferably grown at about 19° C. to 28° C. After the regenerating plants have reached the stage of shoot and root development, they may be transferred to a Greenhouse for further growth and testing.

Genomic DNA may be isolated from callus cell lines and plants to determine the presence of the exogenous gene through the use of techniques well known to those skilled in the art such as PCR and/or Southern blotting.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a construct encoding a DNA binding molecule or target DNA according to the present invention and which is capable of introducing the construct into the genome of an organism, such as a plant.

The vector system may comprise one vector, but it can comprise at least two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301–305 and Butcher D. N. et al. (1980), *Tissue Culture Methods for Plant Pathologists,* eds.: D. S. Ingrams and J. P. Helgeson, 203–208).

Several different Ti and Ri plasmids have been constructed which are suitable for the construction of the plant or plant cell constructs described above.

Examples of Specific Applications

The DNA binding molecule/target DNA/DNA binding ligand combination may be used to regulate the expression of a nucleotide sequence of interest, such as in a cell of an organism, including prokaryotes, yeasts, fungi, plants and animals, for example mammals, including humans.

Nucleotide sequences of interest include genes associated with disease in humans and animals and therapeutic genes. Thus a DNA binding molecule may be used in conjunction with a target DNA sequence and DNA binding ligand in a method of treating or preventing disease in an animal or human patient.

Alternatively, a genetic switch of the invention comprising a DNA binding molecule a target DNA sequence and a DNA binding ligand wherein the DNA binding ligand modulates binding of the DNA molecule to the target DNA may be used to regulate expression of a nucleotide sequence of interest in a plant. Examples of specific applications include the following:

1. Improvement of ripening characteristics in fruit. A number of genes have been identified that are involved in the ripening process (such as in ethylene biosynthesis). Control of the ripening process via regulation of the expression of those genes will help reduce significant losses via spoilage.
2. Modification of plant growth characteristics through intervention in hormonal pathways. Many plant characteristics are controlled by hormones. Regulation of the genes involved in the production of and response to hormones will enable produce crops with altered characteristics.
3. Improvement of other characteristics by manipulation of plant gene expression. Overexpression of the Na+/H+ antiport gene has resulted in enhanced salt tolerance in Arabidopsis. Targetted zinc fingers could be used to regulate the endogenous gene.
4. Improvement of plant aroma and flavour. Pathways leading to the production of aroma and flavour compounds in vegetables and fruit are currently being elucidated allowing the enhancement of these traits using gene switch technology.
5. Improving the pharmaceutical and nutraceutical potential of plants. Many pharmaceutically active compounds are known to exist in plants, but in many cases production is limited due to insufficient biosynthesis in plants. Gene switch technology could be used to overcome this limitation by upregulating specific genes or biochemical pathways. Other uses include regulating the expression of genes involved in biosynthesis of commercially valuable compounds that are toxic to the development of the plant.
6. Reducing harmful plant components. Some plant components lead to adverse allergic reaction when ingested in food. Gene switch technology could be used to overcome this problem by downregulating specific genes responsible for these reactions.
7. As well as modulating the expression of endogenous genes, heterologous genes may be introduced whose expression is regulated by a gene switch of the invention. For example, a nucleotide sequence of interest may encode a gene product that is preferentially toxic to cells of the male or female organs of the plant such that the ability of the plant to reproduce can be regulated. Alternatively, or in addition, the regulatory sequences to which the nucleotide sequence is operably linked may be tissue-specific such that expression when induced only occurs in male or female organs of the plant. Suitable sequences and/or gene products are described in WO89/10396, WO92/04454 (the TA29 promoter from tobacco) and EP-A-344,029, EP-A-412,006 and EP-A-412,911.

Other uses include regulating the expression of genes involved in biosynthesis of commercially valuable compounds that are toxic to the development of the plant.

The present invention will now be described by way of the following examples, which are illustrative only and non-limiting. The examples refer to the figures:

EXAMPLES

Example 1

Preparation and Screening of a Zinc Finger Phage Display Library

Selection Of Zinc Finger Phage Binding DNA Targets In The Presence Of Small Molecules Example 1.1

Selection of Zinc Finger Phage that Bind DNA in the Presence of Distamycin A

A powerful method of selecting DNA binding proteins is the cloning of peptides (Smith (1985) Science 228, 1315–1317), or protein domains (McCafferty et al., (1990) Nature 348:552–554; Bass et al., (1990) Proteins 8:309–314), as fusions to the minor coat protein (pIII) of bacteriophage fd, which leads to their expression on the tip of the capsid. A phage display library is created comprising variants of the middle finger from the DNA binding domain of Zif268.

Materials and Methods
Construction and Cloning of Genes

In general, procedures and materials are in accordance with guidance given in Sambrook et al., Molecular Cloning. A Laboratory Manual, Cold Spring Harbor, 1989. The gene for the Zif268 fingers (residues 333–420) is assembled from 8 overlapping synthetic oligonucleotides (see Choo and Klug, (1994) PNAS (USA) 91:11163–67), giving SfiI and NotI overhangs. The genes for fingers of the phage library are synthesised from 4 oligonucleotides by directional end to end ligation using 3 short complementary linkers, and amplified by PCR from the single strand using forward and backward primers which contain sites for NotI and SfiI respectively. Backward PCR primers in addition introduce Met-Ala-Glu as the first three amino acids of the zinc finger peptides, and these are followed by the residues of the wild type or library fingers as required. Cloning overhangs are produced by digestion with SfiI and NotI where necessary. Fragments are ligated to 1 μg similarly prepared Fd-Tet-SN vector. This is a derivative of fd-tet-DOG1 (Hoogenboom et al., (1991) Nucleic Acids Res. 19, 4133–4137) in which a section of the pelB leader and a restriction site for the enzyme SfiI (underlined) have been added by site-directed mutagenesis using the oligonucleotide:

5' CTCCTGCAGTTGGACCTGTGCCAT<u>GGCCGGCTGG</u> (Seq ID No.1)
GCCGCATAGAATGGAACAACTAAAGC 3' which anneals in the region of the polylinker. Electrocompetent DH5α cells are transformed with recombinant vector in 200 ng aliquots, grown for 1 hour in 2×TY medium with 1% glucose, and plated on TYE containing 15 μg/ml tetracycline and 1% glucose.

The zinc finger phage display library of the present invention contains amino acid randomisations in putative base-contacting positions from the second and third zinc fingers of the three-finger DNA binding domain of Zif268, and contains members that bind DNA of the sequence XXXXXGGCG where X is any base. Further details of the library used may be found in WO 98/53057, which is incorporated herein by reference. The DNA sequences A AAAAAGGCG (SEQ ID NO:14) and AAAAAAGGC-GAAAAAA (SEQ ID NO:15) are used as selection targets in this example because short runs of adenines can cause intrinsic DNA bending—moreover, the structure of the bend can be disrupted by binding of the antibiotic distamycin A.

Phage Selection

Bacterial colonies containing zinc finger phage libraries are transferred from plates to 200 ml 2×TY medium (16 g/liter Bactotryptone, 10 g/liter Bactoyeast extract, 5 g/liter NaCl) containing 50 μM ZnCl$_2$ and 15 μg/ml tetracycline. Bacterial cultures are grown overnight at 30° C. Culture supernatant containing phages is obtained by centrifuging at 1500×g for 5 minutes.

Phage selection is over 4 rounds. Before each round, a pre-selection step is included comprising binding of 10 pmol of biotinylated DNA target sites immobilised on 50 mg streptavidin coated beads (Dynal) to 1 ml of phage solution (bacterial culture supernatant diluted 1:1 with PBS containing 50 μM ZnCl$_2$, 4% Marvel, 2% Tween), for 1 hour at 20° C. on a rolling platform. After this time, 0.5 ml of phage solution is transferred to a streptavidin coated tube and incubated with 2 pmol biotinylated DNA target site in the presence of 2 μM distamycin A (Sigma) and 4 μg poly [d(I-C)]. After a one hour incubation the tubes are washed 20 times with PBS containing 50 μM ZnCl$_2$ and 1% Tween, and 3 times with PBS containing 50 μM ZnCl$_2$. Phage are eluted using 0.1 ml 0.1 M triethylamine and the solution is neutralised with an equal volume of 1M Tris-Cl (pH 7.4). Logarithmic-phase *E. coli* TG1 cells are infected with eluted phage, and grown overnight, as described above, to prepare phage supernatants for subsequent rounds of selection.

After 4 rounds of selection, bacteria are plated and phage prepared from 96 colonies are screened for binding to the DNA target site in the presence and absence of distamycin A. Binding reactions are carried out in wells of a streptavidin-coated microtitre plate (Boehringer Mannheim) and contain 50 μl of phage solution (bacterial culture supernatant diluted 1:1 with PBS containing 50 μM ZnCl$_2$, 4% Marvel, 2% Tween), 0.15 pmol DNA target site and 0.25 μg poly [d(I-C)]. When added, distamycin A is present at a concentration of 2 μM. After a one hour incubation the wells are washed 20 times with PBS containing 50 μM ZnCl$_2$ and 1% Tween (and also distamycin A at a concentration of 2 μM where appropriate), and 3 times with PBS containing 50 μM ZnCl$_2$. Bound phage are detected by ELISA (carried out in the presence of distamycin A at a concentration of 2 μM where appropriate) with horseradish peroxidase-conjugated anti-M13 IgG (Pharmacia Biotech) and quantitated using SOFTMAX 2.32 (Molecular Devices).

Sequencing of Selected Phage

Single colonies of transformants obtained after four rounds of selection as described, are grown overnight in 2×TY/Zn/Tet. Small aliquots of the cultures are stored in 15% glycerol at −20° C., to be used as an archive. Single-stranded DNA is prepared from phage in the culture supernatant and sequenced using the Sequenase™ 2.0 kit (U.S. Biochemical Corp.). The amino acid sequences of the zinc finger clones are deduced.

Amino acid sequences from helical regions of zinc fingers selected to bind DNA in the presence of distamycin

| | F1 -1123456 | SEQ ID NO | F2 -1123456 | SEQ ID NO | F3 -1123456 | SEQ ID NO |
|---|---|---|---|---|---|---|
| Clone 1 | RSDELTR | 16 | RSDDLST | 17 | TNNTRIK | 20 |
| Clone 2 | RSDELTR | 16 | RSDDLST | 17 | HKATRIK | 21 |
| Clone 3 | RSDELTR | 16 | RSDDLST | 17 | TDKVRKK | 22 |
| Clone 4 | RSDELTR | 16 | RSDDLST | 17 | HNASRIN | 23 |
| Clone 5 | RSDELTR | 16 | RSDDLSV | 18 | TNNSRKK | 24 |
| Clone 6 | RSDELTR | 16 | RSDDLST | 17 | TNATRKK | 25 |
| Clone 7 | RSDELTR | 16 | RSDDLSQ | 19 | TRNTRKN | 26 |
| Clone 8 | RSDELTR | 16 | RSDDLSV | 18 | TNNSRKN | 27 |

Zinc finger phage clones are isolated according to this method which bind the target with higher affinity in the presence of ligand than in the absence of ligand (see FIG. 1). This method also selected certain clones that bound DNA in the absence of the ligand but were displaced from the DNA in the presence of the ligand (see Example 1.4 below).

Example 1.2
Selection of Zinc Finger Phage Binding DNA in the Presence of Actinomycin D An adaptation to the method outlined in the Example 1.1 was used to isolate phage that bound DNA in the presence of a different small molecule, actinomycin D. In this example the DNA target was AGCTTGGCG.

Phage Selection

Essentially the method was the same as used in the previous section using four rounds of a preselection step followed by a selection step, washing and elution. Differences in the method are described. The preselection step comprised of 7.5 pmol of biotinylated DNA target site immobilised on 18.75 µl streptavidin coated beads (Dynal) in a 100 µl mixture containing 4 µl phage library 96 µl PBS, 2% Marvel, 1% Tween-20, 50 µM ZnCl$_2$ for 1 hour at room temperature with constant mixing. Phage selections were made in streptavidin coated tubes with the phage supernatant, 5 nM biotinylated target DNA, 10 µM actinomycin D in the presence of 1 µg poly [d(I-C)] competitor. The selections were incubated for 1 hour at room temperature. The bound phage were washed and eluted as described above.

ELISA was performed as described above but using 5 nM biotinylated target DNA, 0.25 µg poly[d(I-C)] competitor in the assay and 10 µM actinomycin D where appropriate. Phage were sequenced using Big Dye Terminator Cycle Sequencing Kit (Perkin Elmer Biosystems) and automated sequencing.

The amino acid sequences from the helical regions of the selected zinc fingers were sequenced as:

```
clone 1   RSDELTRHIRIH      RSDTLSVHIRTH      HNAHRKTHTKIH
          (SEQ ID NO:30)    (SEQ ID NO:31)    (SEQ ID NO:32)

clone 6   RSDELTRHIRIH      RSDHLSVHIRTH      KKFAHSAHRKTHTKIH
          (SEQ ID NO:30)    (SEQ ID NO:33)    (SEQ ID NO:34)
```

These two clones were selected using the oligo:

tatacaAGCTTGGCGatcacagtcagtccacacgtc (SEQ ID NO:35)

Figure 2:
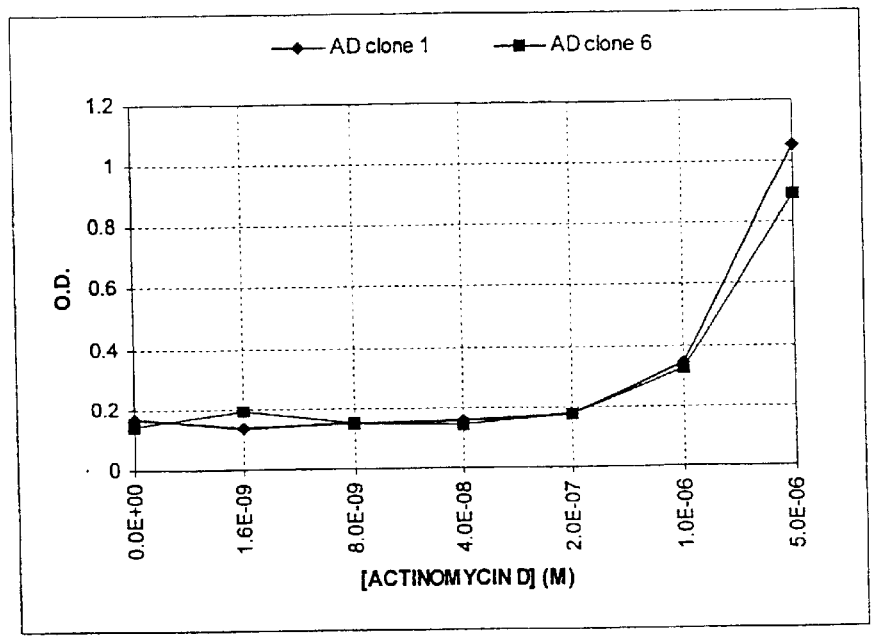
FIG. 2 shows a graph of the effect of Actinomycin D concentration on binding of two different phage (AD clone 1 and 6) to the DNA sequence AGCTTGGCG. In this case, the small molecule causes phage binding to DNA.

These zinc finger clones bind to the target oligo with higher affinity in the presence of actinomycin D than in the absence of DNA binding ligand (see FIG. 2).

Example 1.3
Selection of Zinc Finger Phage Using Randomised DNA in the Presence of Echinomycin. And Subsequent Deconvolution of Binding Partners In this experiment the library of DNA binding molecules was sorted using a library of DNA sequences in the presence of a small molecule. After DNA binding molecules that bound to DNAs in the presence of the small molecule had been selected, the optimal binding site(s) for each DNA binding molecule were determined using the binding site signature.

a) Selections

In this experiment, 50 pmol of DNA target library of sequence YRYRYGGCG (where Y is C or T and R is G or A) was bound to 125 µl of streptavidin coated beads (Dynal) and the beads were used to preselect 0.4 µl of phage library in 100 µl of PBS, 2% Marvel, 1% Tween-20, 50 µM ZnCl$_2$ for 1 hour at room temperature with constant mixing. Phage selections were made in streptavidin coated tubes with the phage supernatant, 30 nM biotinylated target DNA, 10 µM echinomycin in the presence of 1 µg poly [d(I-C)] competitor. The selections were incubated for 1 hour at room temperature. The bound phage were washed and eluted as described above.

ELISA was performed as described above but using 30 nM biotinylated target DNA, 0.5 µg poly[d(I-C)] competitor in the assay and 10 µM echinomycin where appropriate. Phage were sequenced using Big Dye Terminator Cycle Sequencing Kit (Perkin Elmer Biosystems) and automated sequencing.

Figure 3:
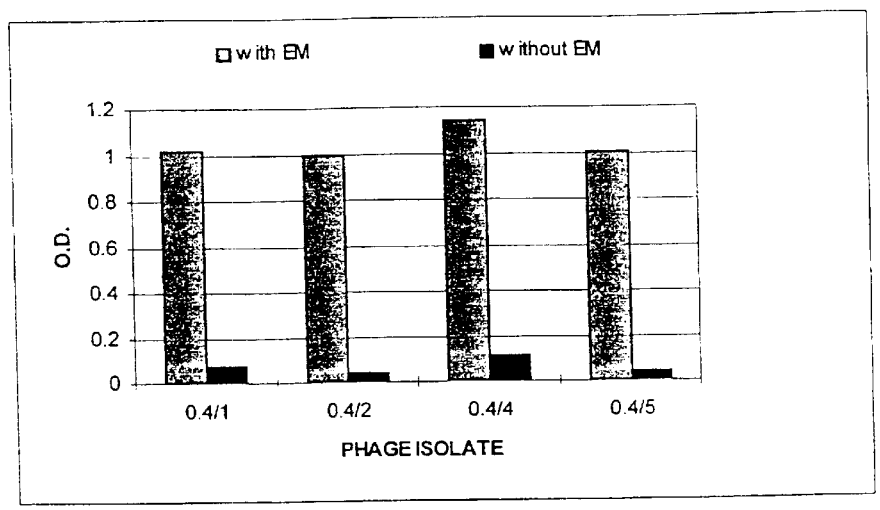
FIG. 3 shows four different phage (0.4/1, 0.4/2, 0.4/4 and 0.4/5) binding to randomised DNA oligo YRYRYGGCG (where Y is C or T and R is G or A) in the presence, but not in the absence, of echinomycin (EM).

Four different clones were selected using the DNA library tatagtYRYRYGGCG atcacagtcagtccacacgtc (SEQ ID NO:36) in the presence of echinomycin (see FIG. 3).

The amino acid sequences from the helical regions of the selected zinc fingers were sequenced as:

```
clone    RSDELTRHIRIH      RSDHLSKHIRTH      KKFARSQTRINHTKIH
0.4/1    (SEQ ID NO:30)    (SEQ ID NO:37)    (SEQ ID NO:38)

clone    RSDELTRHIRIH      RSDHLSEHIRTH      TRNARTKHTKIH
0.4/2    (SEQ ID NO:30)    (SEQ ID NO:39)    (SEQ ID NO:40)

clone    RSDELTRHIRTH      RSDHLSNHIRTH      RNDTRKTHTKIH
0.4/4    (SEQ ID NO:30)    (SEQ ID NO:41)    (SEQ ID NO:42)

clone    RSDELTRHIRIH      RSDNLSTHIRTH      KKFAHSNTRKNHTKIH
0.4/5    (SEQ ID NO:30)    (SEQ ID NO:43)    (SEQ ID NO:44)
``` b) Binding site signature

The signature of the clone 0.4/4 was determined using a modified binding site signature assay. For each of the 5 randomised positions of the oligo, a base was fixed at one of the five positions whilst the remaining 4 positions contained defined mixtures of bases. For the pyrimidine position the base was fixed as either C or T and for the purine position the base was fixed as either G or A so that by testing each position in turn an optimal sequence or binding site signature could be determined.

In each well of a streptavidin-coated microtitre plate 2 µl of phage solution (overnight E. coli culture supernatant containing phage) were mixed with 48 μl of 2% Marvel, 1% Tween-20, 0.5 μg poly [d(I-C)], 10 μM echinomycin and between 8–16 nM of biotinylated target DNA. The reaction was incubated for 1 hour at room temperature, followed by 6 washes with PBS containing 1% Tween-20, 50 μM $ZnCl_2$ and 3 washes with PBS containing 0.05% Tween-20, 50 μM $ZnCl_2$. 100 μl of PBS containing 1% Marvel, 0.05% Tween-20, 50 μM $ZnCl_2$ and 1/5000 dilution of anti-M13 horse radish peroxidase antibody conjugate (Amersham Pharmacia Biotech) was added to each well and incubated for 1 hour at room temperature. The ELISA plate was washed 3 times with PBS containing 0.05% Tween-20, 50 μM $ZnCl_2$ followed by three washes with 3 washes of PBS containing 50 μM $ZnCl_2$. The assay was developed with BCIP/NBT substrates and quantified using a plate reader.

Figure 4:
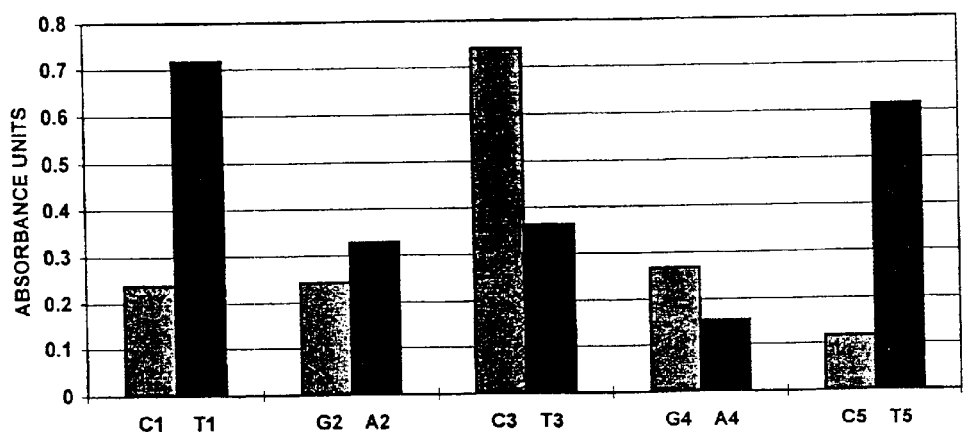
FIG. 4 shows the binding site signature of phage 0.4/4 selected using the randomized DNA sequence (Y1)(R2)(Y3)(R4)(Y5)GGCG. The phage has a preference for the DNA sequence (T)/(G/A)(C)(G/A)(T) in the presence of echinomycin.

This method determined the binding site sequence of clone 0.4/4 to be $(T_1)(G/A_2)(C_3)(G/A_4)(T_5)$ (see FIG. 4).

c) Verification of the target DNA sequence

The optimal target DNA sequence, as determined by the binding site signature, was synthesised together with two other related DNA sequences that were present in the original random DNA library but differed in some of the optimal base positions of the binding site.

These oligonucleotides had the sequence:

```
tatagtTACGTGGCGatcacagtcagtccacacgtc (SEQ ID NO:45)

tatagtTGTatGGCGatcacagtcagtccacacgtc (SEQ ID NO:46)

tatagtCGTACGGCGatcacagtcagtccacacgtc (SEQ ID NO:47)
```

Binding of the phage clone was tested as a function of DNA concentrations (from 5 nM to 0.312 nM) in the presence of 10 μM echinomycin. A phage ELISA was set up using 20 μl phage supernatant, 0.5 μg poly[d(I-C)], 10 μM echinomycin in PBS containing 1% Marvel, 1% Tween-20, 50 μM $ZnCl_2$. The total volume of the assay was 50 μl. The assay was washed and developed as described as for the binding site signature assay.

Figure 5:
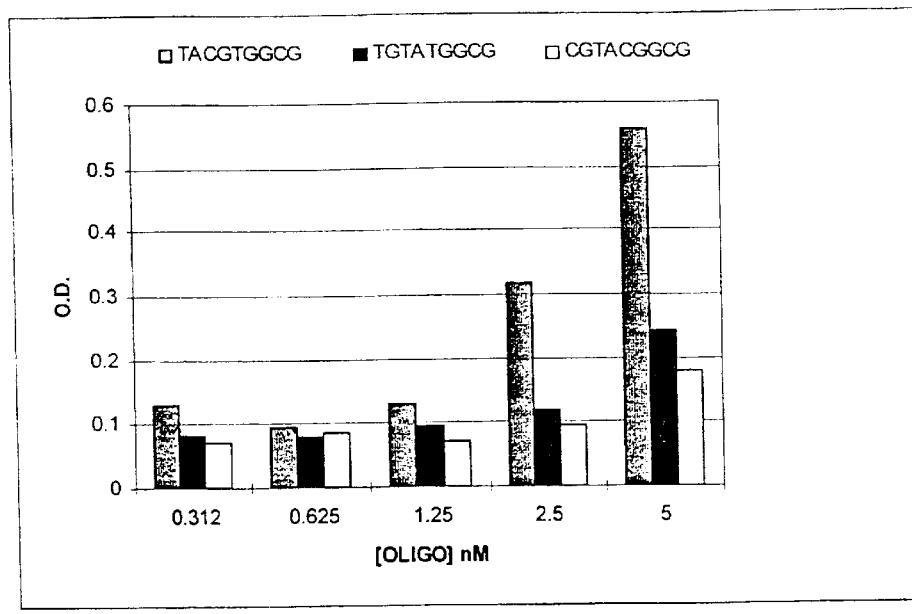
FIG. 5 shows binding of the phage 0.4/4 to three related DNA sequences, TACGTGGCG, TGTATGGCG and CGTACGGCG, as a function of echinomycin concentration. The first DNA site contains the optimal binding sequence as revealed by the binding site signature.

This method showed that the clone 0.4/4 bound preferentially to the sequence determined from the binding site signature, i.e. TACGTGGCG, in the presence of the small molecule (see FIG. 5).

Example 1.4
Selection of Zinc Finger Phage that are Dissociated from their DNA Targets in the Presence of Distamycin A or Actinomycin D This example describes phage that bound DNA targets with higher affinity in the absence of ligand. These phage were isolated using either: (a) the same method as in example 1.1, or (b) by selection in the absence of small molecule and phage elution from DNA using a small molecule.

In this latter case (b) the method was as follows.
Phage selection is over 4 rounds. Binding reactions contain 10 pmol biotinylated DNA site immobilised on 50 mg streptavidin coated beads (Dynal) and a 1 ml solution of zinc finger phage library (as described in 1.1) Reactions were incubated for 1 h on a rolling platform. After this time, beads were washed 20 times as described in 1.1 and finally phage were eluted from the beads over 5 minutes using a solution containg ligand (10 μM Distamycin A, or 1 μM Actinomycin D in PBS/Zn).

Some phage isolated by either of the above methods (a or b) bound DNA in the absence of ligand but could be displaced by concentrations of distamycin A at 10 μM and actinomycin D at 1 μM. The distamycin sensitive clone was selected using the DNA target AAAAAGCGGAAAAA (SEQ ID NO:48) and its helices were sequenced as:

| QSRSLIQ | QRDSLSR | RSDERKR |
|---|---|---|
| (SEQ ID NO:49) | (SEQ ID NO:50) | (SEQ ID NO:51) |

The actinomycin D sensitive clone was selected with the DNA target AGCTTGGCG and its helices were sequenced as:

| RSDELTR | RSDVLST | TRSSRKK |
|---|---|---|
| (SEQ ID NO:16) | (SEQ ID NO:52) | (SEQ ID NO:53) |

Figure 6:
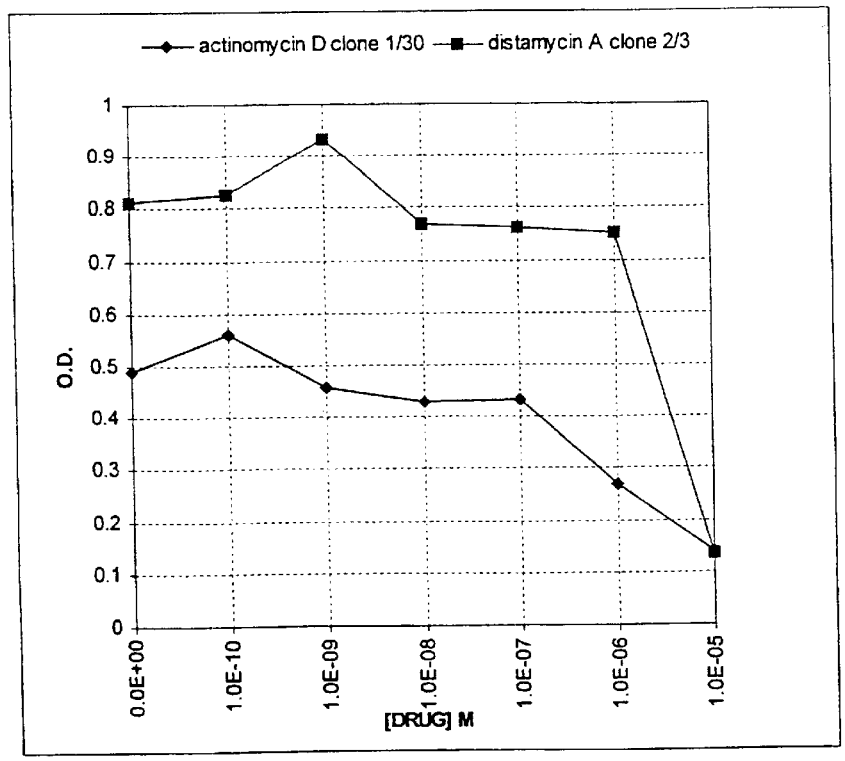
FIG. 6 shows a graph of the effect of ligand concentration on binding of two different phage to specific DNA sequences. In this case, the respective phage are dissociated from the DNA in the presence of distamycin A or actinomycin D.

FIG. 6 demonstrates the sensitivity of each clone to the respective drug.

Example 2
Modulation of Binding of Polypeptides to Target DNA by DNA Binding Ligand Individual phage clones are assayed for modulation of target DNA binding by ligand in a phage ELISA binding assay.

Binding assay reactions are carried out in wells of a streptavidin-coated microtitre plate (Boehringer Mannheim) as in Example 1, except that the distamycin concentration is varied while the DNA concentration is kept constant at 2 nM.

Induction of higher affinity DNA binding is observed when distamycin is added to the binding reaction at $10^{-6}M–10^{-7}M$.

Binding of the zinc finger phage to DNA in the absence of ligand, or at ligand concentrations of $10^{-9}$ M or lower, results in phage retention close to background level, i.e. lower affinity binding than in the presence of ligand.

Background level affinity binding is defined as the phage retention in binding reactions that contain no DNA binding site.

Example 3
DNA-ligand Modulatable Restriction Enzyme

Phage-selected or rationally designed zinc finger domains which bind target DNA sequences in a manner modulatable by a DNA binding ligand can be converted to restriction enzymes which cleave DNA containing said target sequences in a manner modulatable by DNA binding ligand. This is achieved by coupling an appropriate zinc finger, as isolated in Example 1 above, to a cleavage domain of a restriction enzyme or other nucleic acid cleaving moiety.

A method of converting zinc finger DNA binding domains to chimaeric restriction endonucleases has been described in Kim, et al., (1996) Proc. Nati. Acad. Sci. USA 93:1156–1160. In order to demonstrate the applicability of DNA ligand-modulatable zinc fingers to restriction enzymes, a fusion is made between the catalytic domain of Fok I as described by Kim et al. and a zinc finger of Example 1. Fusion of the zinc finger nucleic acid-binding domain to the catalytic domain of Fok I restriction enzyme results in a novel endonuclease which cleaves DNA adjacent to the DNA recognition sequence of the zinc finger (A AAAAAGGCG (SEQ ID NO:14) or AAAAAAGG-CGAAAAAA (SEQ ID NO:15)).

The oligonucleotides AAAAAAGGCG (SEQ ID NO:14) and AAAAAAGGCGAAAAAA (SEQ ID NO:15) are synthesised and ligated to arbitrary DNA sequences. After incubation with the zinc finger restriction enzyme, the nucleic acids are analysed by gel electrophoresis. Bands indicating cleavage of the nucleic acid at a position corresponding to the location of the oligonucleotide(s) (A AAAAAGGCG (SEQ ID NO:14)/AAAAAAGGCG-AAAAAA (SEQ ID NO:15)) are visible.

In a further experiment, the zinc finger is fused to an amino terminal copper/nickel binding motif. Under the correct redox conditions (Nagaoka, M., et al., (1994) J. Am. Chem. Soc. 116:4085–4086), sequence-specific DNA cleavage is observed, only in the presence of DNA incorporating oligonucleotide AAAAAAGGCG (SEQ ID NO:14) or A AAAAAGGCGAAAAAA (SEQ ID NO:15).

Example 4
Modulation of Transcriptional Activity in vivo

A reporter system is produced which produces a reporter signal conditionally depending on the binding of the zinc finger DNA binding molecule to its target DNA sequence. This binding, and hence transcription from the reporter system, is modulated by the DNA binding ligand Distamycin A.

A transient transfection system using zinc finger transcription factors is produced as described in Choo, Y., et al., (1997) J. Mol. Biol 273:525–532. This system comprises an expression plasmid which produces a phage-selected zinc finger fused to the activation domain of HSV VP16, and a reporter plasmid which contains the recognition sequence of the zinc finger upstream of a CAT reporter gene.

Thus, a zinc finger which recognises the DNA sequence AAAAAAGGCG (SEQ ID NO:14) is selected by phage display as described in Example 1. By the method of the preceding examples, said zinc finger is used to construct transcription factors as described above.

A transient expression experiment is conducted, wherein the CAT reporter gene on the reporter plasmid is placed downstream of the sequence AAAAAAGGCG (SEQ ID NO:14). The reporter plasmid is cotransfected with a plasmid vector expressing the zinc finger-HSV fusion under the control of a constitutive promoter. No activation of CAT gene expression is observed.

However, when the same experiment is conducted in the presence of Distamycin A, CAT expression is observed as a result of the binding of the zinc finger transcription factor to its recognition sequence AAAAAAGGCG (SEQ ID NO:14).

Example 5
Isolation of Cognate Target Nucleic Acids

Using a known DNA binding molecule, target DNA sequences to which it can bind are isolated.

The 434 repressor is a gene regulatory protein of phage 434. It binds to a 14 bp operator site (see Koudelka et al., 1987, Nature vol 326 pp 886–888). This operator site consists of five conserved bp (1–5), then four variable bp (6–9), then five more conserved bp (10–14) as shown below:

```
(SEQ ID NO:54)
Site:  1        5 6 7 8 9 10        14

Base:  A C A A G/T X X X X A/T T T G T wherein X is any base.
``` wherein X is any base.
The conserved bases contact the 434 repressor protein. The four variable bases are thought not to contact the 434 repressor protein. However, the four bases which do not contact the 434 repressor protein may affect the affinity of binding of the repressor to the operator site.

The 434 repressor protein (ie. the DNA binding molecule) is contacted with a library of different target DNA sequences in the presence and absence of ligand:

The target DNA sequences are synthesized using an Applied Biosystems 380A DNA synthesizer and are purified by gel electrophoresis. The four variable bases ('X' as shown above) are randomised, producing a library of 256 different target DNA molecules, position 5 being T, and position 10 being A. At the 5' and 3' ends of this sequence are placed PCR primer sequences for amplification and recovery of the central target sequences.

Structure of target DNA sequence library:

```
5'                           1  6 9  14               3'   (SEQ ID NO:55)
GTCGGATCCTGTCTGAGGTGAGACAATXXXXATTGTGTCTTCCGACGTCGAATTCGCG
``` wherein X is any base, and the partially randomised 434 operator is underlined.

The 434 repressor protein is added to the library of target DNA sequences, in the presence and absence of 2 µM distamycin A (Sigma) ligand in 200 µl binding buffer (9 mM Tris-HCl pH 8.0, 90 mM KCl, 90 µM ZnSO$_4$) and incubated for 30 min.

Nitrocellulose filters (BA 85, Schleicher and Schüll) are placed into a suction chamber (as in Thiesen et al. (eds), Immunological Methods vol IV, Academic Press, Orlando) and prewet with 600 ml Tris-HCl binding buffer. The protein-oligonucleotide mix is applied to the filter(s) with gentle suction, the filters are washed with 4 ml Tris-HCl binding buffer. Oligonucelotides are eluted in 200 µl binding buffer plus 1 mM 1-10-o-phenanthroline.

Oligonucleotides are then amplified by PCR, using the following primers:

```
                                          (SEQ ID NO:56)
         Primer A 5'-GTCGGATCCTGTCTGAGGTGAG-3'

(SEQ ID NO:57)
         Primer B 5'-CGCGAATTCGACGTCGGAAGAC-3'
``` using an amplification kit (Perkin Elmer Cetus) with the following cycling regime: 93° C. 30 sec; 45° C. 120 sec; 45° C. to 67° C. ramp 60 sec; 67° C. 180 sec for 25 cycles. 1 µl of eluted oligonucleotide material is used as template.

Optionally, the PCR amplified DNA product is then used in further rounds of incubation with the 434 repressor protein, nitrocellulose filter binding, oligonucleotide elution and PCR amplification.

PCR amplified DNA products are then sequenced using standard techniques.

Target DNA sequences are selected which bind the 434 repressor with higher affinity in the presence of ligand than in the absence of ligand. Furthermore, DNA sequences are selected which bind the 434 repressor in the absence of ligand with a higher affinity than in the presence of ligand.

Example 6
Isolation of Ligands Which Affect the Binding of a DNA Binding Molecule to its Cognate DNA Target The 434 repressor protein of Example 5 is used in conjunction with a target operator DNA sequence to which it binds.

The operator sequence used is

5'-ACAATAAATATTGT-3' (SEQ ID NO:58)

A library of DNA binding ligands is used in place of the 2 μM distamycin A (Sigma) DNA binding ligand of Example 5.

Ligands are isolated which are capable of increasing the affinity of the 434 repressor for its cognate DNA target sequence. Ligands are also isolated which are capable of decreasing the affinity of the 434 repressor for its cognate DNA target sequence.

Example 7
Generation of Transgenic Plants Expressing a Zinc Finger Protein Fused to a Transactivation Domain To investigate the utility of heterologous zinc finger proteins for the regulation of plant genes, a synthetic zinc finger protein was designed and introduced into transgenic *Arabidopsis thaliana* under the control of a promoter capable of expression in a plant as described below. A second construct comprising the zinc finger protein binding sequence fused upstream of the Green Fluorescent Protein (GFP) reporter gene was also introduced into transgenic *Arabidopsis thaliana* as described in Example 8. Crossing the two transgenic lines produced progeny plants carrying both constructs in which the GFP reporter gene was expressed demonstrating transactivation of the gene by the zinc finger protein.

Using conventional cloning techniques, the following constructs were made as XbaI-BamHI fragments in the cloning vector pcDNA3.1 (Invitrogen).

pTFIIIAZifVP16 pTFIIIAZifVP16 comprises a fusion of four finger domains of the zinc finger protein TFIIIA fused to the three fingers of the zinc finger protein Zif268. The TFIIIA-derived sequence is fused in frame to the translational initiation sequence ATG. The 7 amino acid Nuclear Localization Sequence (NLS) of the wild-type Simian Virus 40 Large T-Antigen is fused to the 3' end of the Zif268 sequence, and the VP16 transactivation sequence is fused downstream of the NLS. In addition, 30 bp sequence from the c-myc gene is introduced downstream of the VP16 domain as a "tag" to facilitate cellular localization studies of the trangene. While this is experimentally useful, the presence of this tag is not required for the activation (or repression) of gene expression via zinc finger proteins.

The sequence of pTFIIIAZifVP16 is shown in SEQ ID No. 1 as an XbaI-BamHI fragment. The translational initiating ATG is located at position 15 and is double underlined. Fingers 1 to 4 of TFIIIA extend from position 18 to position 416. Finger 4 (positions 308–416) does not bind DNA within the target sequence, but instead serves to separate the first three fingers of TFIIIA from Zif268 which is located at positions 417–689. The NLS is located at positions 701–722, the VP16 transactivation domain from positions 723–956, and the c-myc tag from positions 957–986. This is followed by the translational terminator TAA.

pTFIIIAZifVP64 pTFIIIAZifVP64 is similar to pTFIIIAZifVP16 except that the VP64 transactivation sequence replaces the VP16 sequence of pTFIIIAZifVP16.

The sequence of pTFIIIAZifVP64 is shown in SEQ ID No. 2 as an XbaI-BamHI fragment. Locations within this sequence are as for pTFIIIAZifVP16 except that the VP64 domain is located at position 723–908 and the c-myc tag from positions 909–938.

Using conventional cloning techniques, the sequence 5'-AAGGAGATATAACA-3'(SEQ ID NO:59) is introduced upstream of the translational initiating ATG of both pTFIIIAZifVP16 and pTFIIIAZifVP64. This sequence incorporates a plant translational initiation context sequence to facilitate translation in plant cells (Prasher et al. Gene 111: 229–233 (1992); Chalfie et al. Science 263: 802–805 (1992)).

The final constructs are transferred to the plant binary vector pBIN121 between the Cauliflower Mosaic Virus 35S promoter and the nopaline synthase terminator sequence. This transfer is effected using the XbaI site of pBIN121. The binary constructs thus derived are then introduced into *Agrobacterium tumefaciens* (strain LBA 4044 or GV 3101) either by triparental mating or direct transformation.

Next, *Arabidopsis thaliana* are transformed with Agrobacterium containing the binary vector construct using conventional transformation techniques. For example, using vacuum infiltration (e.g. Bechtold et al. CR Acad Sci Paris 316: 1194–1199; Bent et al. Science 265: 1856–1860 (1994)), transformation can be undertaken essentially as follows. Seeds of Arabidopsis are planted on top of cheesecloth covered soil and allowed to grow at a final density of 1 per square inch under conditions of 16 hours light/8 hours dark. After 4–6 weeks, plants are ready to infiltrate. An overnight liquid culture of Agrobacterium carrying the appropriate construct is grown up at 28° C. and used to inoculate a fresh 500 ml culture. This culture is grown to an $OD_{600}$ of at least 2.0, after which the cells are harvested by centrifugation and resuspended in 1 liter of infiltration medium (1 liter prepared to contain: 2.2 g MS Salts, 1×B5 vitamins, 50 g sucrose, 0.5 g MES pH 5.7, 0.044 μM benzylaminopurine, 200 L Silwet μL-77 (OSI Specialty)). To vacuum infiltrate, pots are inverted into the infiltration medium and placed into a vacuum oven at room temperature. Infiltration is allowed to proceed for 5 mins at 400 mm Hg. After releasing the vacuum, the pot is removed and layed it on its side and covered with Saran wrap. The cover is removed the next day and the plant stood upright. Seeds harvested from infiltrated plants are surface sterilized and selected on appropriate medium. Vernalizalizion is undertaken for two nights at around 4° C. Plates are then transferred to a plant growth chamber. After about 7 days, transformants are visible and are transferred to soil and grown to maturity.

Many transgenic plants are grown to maturity. They appear phenotypically normal and are selfed to homozygosity using standard techniques involving crossing and germination of progeny on appropriate concentration of antibiotoic.

Transgenic plant lines carrying the TFIIIAZifVP16 construct are designated At-TFIIIAZifVP16 and transgenic plant lines carrying the TFIIIAZifVP64 construct are designated At-TFIIIAZifVP64.

Example 8
Generation of Transgenic Plants Carrying a Green Fluorescent Protein Reporter Gene A reporter plasmid is constructed which incorporates the target DNA sequence of the TFIIIAZifVP16 and TFIIIAZifVP64 zinc finger proteins described above upstream of the Green Fluorescent Protein (GFP) reporter gene. The target DNA sequence of TFIIIAZifVP16 and TFIIIAZifVP64 is shown in SEQ I.D. No. 3. This sequence is incorporated in single copy immediately upstream of the CaMV 35S–90 minimal promoter to which the GFP gene is fused.

The resultant plasmid, designated pTFIIIAZif-UAS/GFP, is transferred to the plant binary vector pBIN121 replacing the Cauliflower Mosaic Virus 35S promoter. This construct is then transferred to *Agrobacterium tumefaciens* and subsequently transferred to *Arabidopsis thaliana* as described above. Transgenic plants carrying the construct are designated At-TFIIIAZif-UAS/GFP.

Example 9
Use of Zinc Finger Proteins to Up-regulate a Transgene in a Plant

To assess whether the zinc finger constructs TFIIIAZifVP16 and TFIIIAZifVP64 are able to transactivate gene expression in planta, Arabidopsis lines At-TFIIIAZifVP16 and At-TFIIIAZifVP64 are crossed to At-TFIIIAZif-UAS/GFP. The progeny of such crosses yield plants that carry the reporter construct TFIIIAZif-UAS/GFP together with either the zinc finger protein construct TFIIIAZifVP16 or the zinc finger construct TFIIIAZifVP64.

Plants are screened for GFP expression using an inverted fluorescence microscope (Leitz DM-IL) fitted with a filter set (Leitz-D excitation BP 355–425, dichronic 455, emission LP 460) suitable for the main 395 nm excitation and 509 nm emission peaks of GFP.

In each case, the zinc finger construct is able to transactivate gene expression demonstrating the utility of heterologous zinc finger proteins for the regulation of plant genes.

Example 10
Generation of Transgenic Plants Expressing a Zinc Finger Fused to a Plant Transactivation Domain The constructs pTFIIIAZifVP16 and pTFIIIAZifVP64 utilize the VP16 and VP64 transactivation domains of Herpes Simplex Virus to activate gene expression. Alternative transactivation domains are various and include the C1 transactivation domain sequence (from maize; see Goff et al.; Genes Dev. 5: 298–309 (1991); Goff et al.; Genes Dev. 6: 864–875 (1992)), and a number of other domains that have been reported from plants (see Estruch et al.; Nucl. Acids Res. 22: 3983–3989 (1994)).

Construct pTFIIAZifC1 is made as described above for pTFIIIAZifVP16 and pTFIIIAZifVP64 except the VP16/VP64 activation domains are replaced with the C1 transactivation domain sequence A transgenic Arabidopsis line, designated At-TFIIAZifC1, is produced as described above in Example 8 and crossed with At-TFIIIAZif-UAS/GFP. The progeny of such crosses yield plants that carry the reporter construct TFIIIAZif-UAS/GFP together with either the zinc finger protein construct TFIIIAZifC1.

Plants are screened for GFP expression using an inverted fluorescence microscope (Leitz DM-IL) fitted with a filter set (Leitz-D excitation BP 355–425, dichronic 455, emission LP 460) suitable for the main 395 nm excitation and 509 nm emission peaks of GFP.

Example 11
Regulation of an Endogenous Plant Gene—UDP Glucose Flavonoid Glucosyl-transferase (UFGT).

To determine whether a suitably configured zinc finger could be used to regulate gene transcription from an endogenous gene in a plant, the maize UDP glucose flavonoid glucosyl-transferase (UFGT) gene (the Bronze1 gene) was selected as the target gene. UFGT is involved in anthocyanin biosynthesis. A number of wild type alleles have been identified including Bz-W22 that conditions a purple phenotypes in the maize seed and plant. The Bronze locus has been the subject of extensive genetic research because its phenotype is easy to score and its expression is tissue specific and varied (for example aleurone, anthers, husks, cob and roots). The complete sequence of Bz-W22 including upstream regulatory sequences has been determined (Ralston et al., Genetics 119: 185–197). A number of sequence motifs that bind transcriptional regulatory proteins have been identified within the Bronze promoter including sequences homologous to consensus binding sites for the myb- and myc-like proteins (Roth et al., Plant Cell 3: 317–325).

Identification of a Zinc Finder that Binds to the Bronze Promoter

The first step is to carry out a screen for zinc finger proteins that bind to a selected region of the Bronze promoter. A region is chosen just upstream of the AT rich block located at between −88 and −80, which has been shown to be critical for Bz1 expression (Roth et al., supra).

1. Bacterial colonies containing phage libraries that express a library of zinc fingers randomised at one or more DNA binding residues (see Example 1) are transferred from plates to culture medium. Bacterial cultures are grown overnight at 30° C. Culture supernatant containing phages is obtained by centrifugation.
2. 10 pmol of biotinylated target DNA, derived from the Bronze promoter, immobilised on 50 mg streptavidin beads (Dynal) is incubated with 1 ml of the bacterial culture supernatant diluted 1:1 with PBS containing 50 $\mu$M $ZnCl_2$, 4% Marvel, 2% Tween in a streptavidin coated tube for 1 hour at 20° C. on a rolling platform in the presence of 4 $\mu$g poly [d(I-C)] as competitor.
3. The tubes are washed 20 times with PBS containing 50 $\mu$M $ZnCl_2$ and 1% Tween, and 3 times with PBS containing 50 $\mu$M $ZnCl_2$ to remove non-binding phage.
4. The remaining phage are eluted using 0.1 ml 0.1 M triethylamine and the solution is neutralised with an equal volume of 1 M Tris-Cl (pH 7.4).
5. Logarithmic-phase *E. coli* TG1 cells are infected with eluted phage, and grown overnight, as described above, to prepare phage supernatants for subsequent rounds of selection.
6. Single colonies of transformants obtained after four rounds of selection (steps 1 to 5) as described, are grown overnight in culture. Single-stranded DNA is prepared from phage in the culture supernatant and sequenced using the Sequenase™ 2.0 kit (U.S. Biochemical Corp.). The amino acid sequences of the zinc finger clones are deduced.

Construction of a Vector for Expression of the Zinc Finger Clone Fused to a C1 Activation Domain in Maize Protoplasis Using conventional cloning techniques and in a similar manner to Example 7, the construct pZifBz23C1 is made in cloning vector pcDNA3.1 (Invitrogen).

pZifBz23C1 comprises a the three fingers of the zinc finger protein clone ZifBz23 fused in frame to the translational initiation sequence ATG. The 7 amino acid Nuclear Localization Sequence (NLS) of the wild-type Simian Virus 40 Large T-Antigen is fused to the 3' end of the ZifBz23 sequence, and the C1 transactivation sequence is fused downstream of the NLS. In addition, 30 bp sequence from the c-myc gene is introduced downstream of the VP16 domain as a "tag" to facilitate cellular localization studies of the trangene.

The coding sequences of pZifBz23C1 are transferred to a plant expression vector suitable for use in maize protoplasts, the coding sequence being under the control of a constitutive CaMV 35S promoter. The resulting plasmid is termed pTMBz23. The vector also contains a hygromycin resistance gene for selection purposes.

A suspension culture of maize cells is prepared from calli derived from embryos obtained from inbred W22 maize stocks grown to flowering in a greenhouse and self pollinated using essentially the protocol described in EP-A-332104 (Examples 40 and 41). The suspension culture is then used to prepare protoplasts using essentially the protocol described in EP-A-332104 (Example 42).

Protoplasts are resuspended in 0.2 M mannitol, 0.1% w/v MES, 72 mM NaCl, 70 mM $CaCl_2$, 2.5 mM KCl, 2.5 mM glucose pH to 5.8 with KOH, at a density of about $2\times10^6$ per ml. 1 ml of the protoplast suspension is then aliquotted into plastic electroporation cuvettes and 10 μg of linearized pTMBz23 added. Electroporation is carried out s described in EP-A-332104 (Example 57). Protoplasts are cultured following transformation at a density of $2\times10^6$ per ml in KM-8p medium with no solidifying agent added.

Measurements of the levels UFGT expression are made using colorimetry and/or biochemical detection methods such as Northern blots or the enzyme activity assays described by Dooner and Nelson, Proc. Natl. Acad. Sci. 74: 5623–5627 (1977). Comparison is made with mock treated protoplasts transformed with a vector only control.

Alternatively, or in addition to, analysing expression of UFGT in transformed protoplasts, intact maize plants may be recovered from transformed protoplasts and the extent of UFGT expression determined. Suitable protocols for growing up maize plants from transformed protoplasts are known in the art: Electroporated protoplasts are resuspended in Km-8p medium containing 1.2% w/v Seaplaque agarose and 1 mg/l 2,4-D. Once the gel has set, protoplasts in agarose are place in the dark at 26° C. After 14 days, clonies arise from the protoplasts. The agarose containing the colonies is transferred to the surface of a 9 cm diameter petri dish containing 30 ml of N6 medium (EP-A-332,104) containing 2,4-D solidified with 0.24% Gelrite®. 100 mg/l hygromycin B is also added to select for transformed cells. The callus is cultured further in the dark at 26° C. and callus pieces subcultured every two weeks onto fresh solid medium. Pieces of callus may be analysed for the presence of the pTMBz23 construct and/or UFGT expression determined.

Corn plants are regenerated as described in Example 47 of EP-A-332,104. Plantlets appear in 4 to 8 weeks. When 2 cm tall, plantlets are transferred to ON6 medium (EP-A-332, 104) in GA7 containers and roots form in 2 to 4 weeks. After transfer to peat pots plants soon become established and can then be treated as normal corn plants.

Plantlets and plants can be assayed for UFGT expression as described above.

Example 12
Regulation of Gene Expression Using a Chemically Inducible Small Molecule The Zif268 Zinc finger phage display library described in Example 1 is screened using the bronze promoter sequence described in Example 11 and a library of small molecule candidate DNA binding ligands, prescreened to remove non-DNA binding molecules. The protocol used is essentially a modification of Example 1 but using multiple ligands. To increase the number of ligands in the screen, ligands are screened in groups of twenty. Once zinc finger clones are identified that have ligand-dependent DNA binding, a single zinc finger clones is tested for ligand-dependent binding against each individual ligand in the mixture originally selected. In this way, a gene switch comprising a zinc finger clone that binds to a region of the bronze promoter in a manner modulatable by a chemical ligand, the region of the bronze promoter and the chemical ligand itself is identified.

The zinc finger clone is fused to a VP16 transactivation domain and other relevant sequences as described in Example 7. The resulting construct, pZFSelectC1 is transferred to the plant binary vector pBIN121 between the Cauliflower Mosaic Virus 35S promoter and the nopaline synthase terminator sequence. The binary construct thus derived is then introduced into Agrobacterium tumefaciens (strain LBA 4044 or GV 3101) either by triparental mating or direct transformation.

A transgenic Arabidopsis line, designated At-ZFSelectC1, is produced as described above in Example 8.

A further transgenic Arabidopsis line, designated At-BzGUS is produced which comprises a reporter construct containing the E. coli beta-glucuronidase gene (GUS) fused to a −90 minimal 35S promoter to which is operably linked the bronze promoter sequence used in the tripartite screen. Arabidopsis lacks endogenous GUS activity. Further, GUS activity is very stable and expression can be measured accurately using flurometric assays of very small amounts of transformed plant tissue (see Jefferson et al., Embo J. 6: 3901–3907 (1987)).

At-ZFSelectC1 lines are crossed with At-BzGUS lines. The progeny of such crosses yield plants that carry the reporter construct BzGUS together with either the zinc finger protein construct ZFSelectC1.

Plants are grown in a range of concentrations of the chemical ligand and GUS activity in leaf tissue measured as described in Jefferson et al., Embo J. 6: 3901–3907 (1987). GUS activity in non transgenic plants, At-ZFSelectC1 line and At-BzGUS lines in the presence of the chemical ligand is also measured.

Example 13
Tripartite Screen for a Zinc Finger/Target DNA and Small Molecule Ligand and the Use of the Identified Components in Regulating Gene Expression A screen is performed as described in Example 12 except that the target DNA is a randomised library based on the Bronze promoter sequence and the procedure described in Example 1.3 is used to determine the binding site signature of identified clones once a ligand has been selected. Verification of the target DNA sequence is also performed as described in Example 1.3.

A target DNA identified in the screen is introduced into a −90 minimal Ca35S-GUS reporter construct as described in Example 12 and used to produce a transgenic Arabidopsis line. A corresponding zinc finger clone is introduced into an expression construct as described in Example 12 and used to produce a transgenic Arabidopsis line. The two lines are crossed and progeny tested for induction of GUS activity in the presence or absence of the ligand identified in the screen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TFIIIA/Zif-VP16 (SEQ ID NO:1)

```
TFIIIA/Zif-VP16 (SEQ ID NO:1)
TCTAGAGCGCCGCCATGGGAGAGAAGGCGCTGCCGGTGGTGTATAAGCGGTACATCTGCTC

TTTCGCCGACTGCGGCGCTGCTTATAACAAGAACTGGAAACTGCAGGCGCATCTGTGCAAA

CACACAGGAGAGAAACCATTTCCATGTAAGGAAGAAGGATGTGAGAAAGGCTTTACCTCGC

TTCATCACTTAACCCGCCACTCACTCACTCATACTGGCGAGAAAAACTTCACATGTGACTC

GGATGGATGTGACTTGAGATTTACTACAAAGGCAAACATGAAGAAGCACTTTAACAGATTC

CATAACATCAAGATCTGCGTCTATGTGTGCCATTTTGAGAACTGTGGCAAAGCATTCAAGA

AACACAATCAATTAAAGGTTCATCAGTTCAGTCACACACAGCAGCTGCCGTATGCTTGCCC

TGTCGAGTCCTGCGATCGCCGCTTTTCTCGCTCGGATGAGCTTACCCGCCATATCCGCATC

CACACAGGCCAGAAGCCCTTCCAGTGTCGAATCTGCATGCGTAACTTCAGTCGTAGTGACC

ACCTTACCACCCACATCCGCACCCACACAGGCGAGAAGCCTTTTGCCTGTGACATTTGTGG

GAGGAAGTTTGCCAGGAGTGATGAACGCAAGAGGCATACCAAAATCCATTTAAGACAGAAG

GACGCGGCCGCACTCGAGCGGAATTCCGGCCCAAAAAAGAAGAGAAAGGTCGCCCCCCCGA

CCGATGTCAGCCTGGGGGACGAGCTCCACTTAGACGGCGAGGACGTGGCGATGGCGCATGC

CGACGCGCTAGACGATTTCGATCTGGACATGTTGGGGGACGGGGATTCCCCGGGGCCGGGA

TTTACCCCCCACGACTCCGCCCCCTACGGCGCTCTGGATACGGCCGACTTCGAGTTTGAGC

AGATGTTTACCGATGCCCTTGGAATTGACGAGTACGGTGGGGAACAAAAACTTATTTCTGA

AGAAGATCTGTAAGGATCC
```

TFIIIA/Zif-VP64 (SEQ ID NO:2)

```
TFIIIA/Zif-VP64 (SEQ ID NO:2)
TCTAGAGCGCCGCCATGGGAGAGAAGGCGCTGCCGGTGGTGTATAAGCGGTACATCTGCTC

TTTCGCCGACTGCGGCGCTGCTTATAACAAGAACTGGAAACTGCAGGCGCATCTGTGCAAA

CACACAGGAGAGAAACCATTTCCATGTAAGGAAGAAGGATGTGAGAAAGGCTTTACCTCGC

TTCATCACTTAACCCGCCACTCACTCACTCATACTGGCGAGAAAAACTTCACATGTGACTC

GGATGGATGTGACTTGAGATTTACTACAAAGGCAAACATGAAGAAGCACTTTAACAGATTC

CATAACATCAAGATCTGCGTCTATGTGTGCCATTTTGAGAACTGTGGCAAAGCATTCAAGA

AACACAATCAATTAAAGGTTCATCAGTTCAGTCACACACAGCAGCTGCCGTATGCTTGCCC

TGTCGAGTCCTGCGATCGCCGCTTTTCTCGCTCGGATGAGCTTACCCGCCATATCCGCATC

CACACAGGCCAGAAGCCCTTCCAGTGTCGAATCTGCATGCGTAACTTCAGTCGTAGTGACC

ACCTTACCACCCACATCCGCACCCACACAGGCGAGAAGCCTTTTGCCTGTGACATTTGTGG

GAGGAAGTTTGCCAGGAGTGATGAACGCAAGAGGCATACCAAAATCCATTTAAGACAGAAG

GACGCGGCCGCACTCGAGCGGAATTCCGGCCCAAAAAAGAAGAGAAAGGTCGAACTTCAGC

TGACTTCGGATGCATTAGATGACTTTGACTTAGATATGCTAGGATCTGACGCGCTAGACGA

TTTCGATCTGGACATGTTGGGCAGCGATGCTCTGGACAGTTTCGATTTAGATATGCTTGGC

TCGGATGCCCTGGATGACTTCGACCTCGACATGCTGTCAAGTCAGCTGAGCCAGGAACAAA

AACTTATTTCTGAAGAAGATCTGTAAGGATCC
```

TFIII/A/Zif binding site (SEQ ID NO:3)

```
TFIIIA/Zif binding site (SEQ ID NO:3)       65
TgcgtgggcgTGTACCTggatgggagacC
```

What is claimed is:

1. A method of selecting a gene switch, which gene switch comprises (i) a target DNA molecule; (ii) a non-naturally occurring DNA binding molecule which binds to the target DNA molecule in a manner modulatable by a DNA binding ligand; and (iii) the DNA binding ligand, which method comprises:
   (a) contacting one or more candidate target DNA molecule(s) with one or more candidate, non-naturally occurring DNA binding molecules, in the presence of one or more DNA binding ligands;
   (b) selecting a complex comprising a candidate target DNA, a non-naturally occurring DNA binding molecule and a DNA binding ligand;
   (c) isolating and/or identifying the unknown components of the complex;
   (d) comparing the binding of the DNA binding molecule component of the complex to the target DNA component of the complex in the presence and absence of the DNA binding ligand component of the complex; and
   (e) selecting complexes wherein the DNA binding molecule component has a higher affinity for the target DNA in the presence of the DNA binding ligand component than in the absence of the DNA binding ligand component.

2. A method according to claim 1 wherein the DNA binding molecules are provided as a plurality of DNA binding molecules.

3. A method according to claim 2 wherein the DNA binding molecules are provided as a library of DNA binding molecules.

4. A method according to claim 1, wherein the target DNA is provided as a plurality of DNA sequences.

5. A method according to claim 1, wherein the target DNA is provided as a library of DNA sequences, said sequences being related to one another by sequence homology.

6. A method according to claim 1 wherein a plurality of candidate DNA binding ligands are used.

7. A method according to claim 6 wherein one target DNA sequence is used.

8. A method according to claim 6 wherein one of the components isolated and/or identified in step (c) is a DNA binding ligand component.

9. A method according to claim 1 wherein one of the components isolated in step (c) is a DNA binding molecule component.

10. A method of selecting a gene switch which gene switch comprises (i) a target DNA molecule; (ii) a non-naturally occurring DNA binding molecule which binds to the target DNA molecule in a manner modulatable by a DNA binding ligand; and (iii) the DNA binding ligand, which method comprises:
   (a) contacting one or more candidate target DNA molecule(s) with one or more candidate, non-naturally occurring DNA binding molecules;
   (b) selecting a complex comprising a candidate target DNA and a non-naturally occurring DNA binding molecule;
   (c) isolating and/or identifying the unknown components of the complex; and
   (d) comparing the binding of the DNA binding molecule component of the complex to the target DNA component of the complex in the presence and absence of the DNA binding ligand component of the complex, wherein the DNA binding molecule component has a higher affinity for the target DNA in the absence of the DNA binding ligand component than in the presence of the DNA binding ligand component.

11. The method according to claim 1, wherein said candidate DNA binding molecules are polypeptides.

12. The method according to claim 11, wherein said candidate DNA binding molecules are polypeptides at least partly derived from transcription factors.

13. The method according to claim 12, wherein said candidate DNA binding molecules are derived from zinc finger transcription factors.

14. A method according to claim 1, wherein the candidate DNA binding molecules are provided as a phage display library.

15. A method according to claim 1, wherein the DNA binding ligand is selected from Distamycin A, Actinomycin D and echinomycin.

16. A method of regulating transcription, in a cell, from a DNA sequence comprising one or more target sequences to which a non-naturally occurring DNA binding molecule binds in a manner modulatable by a DNA binding ligand, the method comprising the steps of:
   (a) contacting one or more candidate DNA molecule(s) with one or more candidate, non-naturally occurring DNA binding molecules, in the presence of one or more DNA binding ligands;
   (b) selecting a complex comprising a candidate DNA. a non-naturally occurring DNA binding molecule and a DNA binding ligand;
   (c) isolating and/or identifying the unknown components of the complex;
   (d) comparing the binding of the DNA binding molecule component of the complex to the DNA component of the complex in the presence and absence of the DNA binding ligand component of the complex; and
   (e) selecting complexes wherein the DNA binding molecule component has a higher affinity for the DNA in the presence of the DNA binding ligand component than in the absence of the DNA binding ligand component; and
   (f) introducing a DNA binding molecule and a DNA binding ligand, as selected in step (e), into the cell, wherein the DNA binding molecule binds to the target sequence.

17. A method of modulating the expression of a gene in a cell, wherein the gene compnses one or more target sequences, said method comprising
   (a) contacting one or more candidate DNA molecule(s) with one or more candidate, non-naturally occurring DNA binding molecules, in the presence of one or more DNA binding ligands;
   (b) selecting a complex comprising a candidate DNA, a non-naturally occurring DNA binding molecule and a DNA binding ligand;
   (c) isolating and/or identifying the unknown components of the complex;
   (d) comparing the binding of the DNA binding molecule component of the complex to the DNA component of the complex in the presence and absence of the DNA binding ligand component of the complex; and
   (e) selecting complexes wherein the DNA binding molecule component has a higher affinity for the DNA in the presence of the DNA binding ligand component than in the absence of the DNA binding ligand component; and
   (f) introducing a DNA binding molecule and a DNA binding ligand, as selected in step (e), into the cell, wherein the DNA binding molecule binds to the target sequence.

18. A method of modulating the expression of one or more target nucleotide sequences in a host cell, wherein the host cell comprises a nucleic acid sequence capable of directing the expression of an exogenous DNA binding molecule, and further wherein the DNA binding molecule binds to the target sequence in a manner modulatable by a DNA binding ligand, the method comprising:

(a) contacting one or more candidate DNA molecule(s) with one or more candidate, non-naturally occurring DNA binding molecules, in the presence of one or more DNA binding ligands;

(b) selecting a complex comprising a candidate DNA. a non-naturally occurring DNA binding molecule and a DNA binding ligand;

(c) isolating and/or identifying the unknown components of the complex;

(d) comparing the binding of the DNA binding molecule component of the complex to the DNA component of the complex in the presence and absence of the DNA binding ligand component of the complex; and (e) selecting complexes wherein the DNA binding molecule component has a higher affinity for the DNA in the presence of the DNA binding ligand component than in the absence of the DNA binding ligand component; and (f) introducing a DNA binding ligand, as selected in step (e), into the cell.

19. A method according to claim 18 wherein the host cell is a plant cell.

20. The method of claim 11, wherein the DNA binding molecule comprises a library of DNA binding molecules.

21. A method of selecting a gene switch which gene switch comprises (i) a target DNA molecule; (ii) a non-naturally occurring DNA binding molecule which binds to the target DNA molecule in a manner modulatable by a DNA binding ligand; and (iii) the DNA binding ligand, which method comprises:

(a) contacting one or more candidate target DNA molecule(s) with one or more candidate, non-naturally occurring DNA binding molecules;

(b) selecting a complex comprising a candidate target DNA and a non-naturally occurring DNA binding molecule;

(c) isolating and/or identifying the unknown components of the complex; and (d) comparing the binding of the DNA binding molecule component of the complex to the target DNA component of the complex in the presence and absence of the DNA binding ligand component of the complex, wherein the DNA binding molecule component has a higher affinity for the target DNA in the presence of the DNA binding ligand component than in the absence of the DNA binding ligand component.

22. The method of claim 21, wherein the DNA binding molecule comprises a library of DNA binding molecules.

* * * * *

UNITED STATES PATENT AND TRADEMARK OFFICE
CERTIFICATE OF CORRECTION

PATENT NO.    : 6,706,470 B2
DATED         : March 16, 2004
INVENTOR(S)   : Choo et al.

Page 1 of 1

It is certified that error appears in the above-identified patent and that said Letters Patent is hereby corrected as shown below:

<u>Title page,</u>
Item [73], Assignee, please replace "Sangamo BioSciences, Inc., Richmond, CA (US)" with -- Gendaq, Ltd., London, United Kingdom (GB) --.

Signed and Sealed this

Eighteenth Day of January, 2005

JON W. DUDAS
*Director of the United States Patent and Trademark Office*

SEQUENCE LISTING

<160> NUMBER OF SEQ ID NOS: 59

<210> SEQ ID NO 1
<211> LENGTH: 995
<212> TYPE: DNA
<213> ORGANISM: Artificial Sequence
<220> FEATURE:
<223> OTHER INFORMATION: Description of Artificial Sequence:
      TFIIIA/Zif-VP16

<400> SEQUENCE: 1

| | | |
|---|---|---|
| tctagagcgc cgccatggga gagaaggcgc tgccggtggt gtataagcgg tacatctgct | 60 |
| ctttcgccga ctgcggcgct gcttataaca agaactggaa actgcaggcg catctgtgca | 120 |
| aacacacagg agagaaacca tttccatgta aggaagaagg atgtgagaaa ggctttacct | 180 |
| cgcttcatca cttaacccgc cactcactca ctcatactgg cgagaaaaac ttcacatgtg | 240 |
| actcggatgg atgtgacttg agatttacta caaaggcaaa catgaagaag cactttaaca | 300 |
| gattccataa catcaagatc tgcgtctatg tgtgccattt tgagaactgt ggcaaagcat | 360 |
| tcaagaaaca caatcaatta aaggttcatc agttcagtca cacacagcag ctgccgtatg | 420 |
| cttgccctgt cgagtcctgc gatcgccgct tttctcgctc ggatgagctt acccgccata | 480 |
| tccgcatcca cacaggccag aagcccttcc agtgtcgaat ctgcatgcgt aacttcagtc | 540 |
| gtagtgacca ccttaccacc cacatccgca cccacacagg cgagaagcct tttgcctgtg | 600 |
| acatttgtgg gaggaagttt gccaggagtg atgaacgcaa gaggcatacc aaaatccatt | 660 |
| taagacagaa ggacgcggcc gcactcgagc ggaattccgg cccaaaaaag aagagaaagg | 720 |
| tcgcccccc gaccgatgtc agcctggggg acgagctcca cttagacggc gaggacgtgg | 780 |
| cgatggcgca tgccgacgcg ctagacgatt tcgatctgga catgttgggg gacggggatt | 840 |
| ccccgggggcc gggatttacc ccccacgact ccgcccccta cggcgctctg gatacggccg | 900 |
| acttcgagtt tgagcagatg tttaccgatg cccttggaat tgacgagtac ggtggggaac | 960 |
| aaaaacttat ttctgaagaa gatctgtaag gatcc | 995 |

<210> SEQ ID NO 2
<211> LENGTH: 947
<212> TYPE: DNA
<213> ORGANISM: Artificial Sequence
<220> FEATURE:
<223> OTHER INFORMATION: Description of Artificial Sequence:TFIIIA/Zif-
      VP64

<400> SEQUENCE: 2

| | | |
|---|---|---|
| tctagagcgc cgccatggga gagaaggcgc tgccggtggt gtataagcgg tacatctgct | 60 |
| ctttcgccga ctgcggcgct gcttataaca agaactggaa actgcaggcg catctgtgca | 120 |
| aacacacagg agagaaacca tttccatgta aggaagaagg atgtgagaaa ggctttacct | 180 |
| cgcttcatca cttaacccgc cactcactca ctcatactgg cgagaaaaac ttcacatgtg | 240 |
| actcggatgg atgtgacttg agatttacta caaaggcaaa catgaagaag cactttaaca | 300 |
| gattccataa catcaagatc tgcgtctatg tgtgccattt tgagaactgt ggcaaagcat | 360 |
| tcaagaaaca caatcaatta aaggttcatc agttcagtca cacacagcag ctgccgtatg | 420 |
| cttgccctgt cgagtcctgc gatcgccgct tttctcgctc ggatgagctt acccgccata | 480 |
| tccgcatcca cacaggccag aagcccttcc agtgtcgaat ctgcatgcgt aacttcagtc | 540 |
| gtagtgacca ccttaccacc cacatccgca cccacacagg cgagaagcct tttgcctgtg | 600 |

-continued

```
acatttgtgg gaggaagttt gccaggagtg atgaacgcaa gaggcatacc aaaatccatt      660
taagacagaa ggacgcggcc gcactcgagc ggaattccgg cccaaaaaag aagagaaagg      720
tcgaacttca gctgacttcg gatgcattag atgactttga cttagatatg ctaggatctg      780
acgcgctaga cgatttcgat ctggacatgt tgggcagcga tgctctggac gatttcgatt      840
tagatatgct tggctcggat gccctggatg acttcgacct cgacatgctg tcaagtcagc      900
tgagccagga acaaaaactt atttctgaag aagatctgta aggatcc                    947
```

```
<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: TFIIA/Zif
      binding site

<400> SEQUENCE: 3
tgcgtgggcg tgtacctgga tgggagacc                                        29
```

```
<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: zinc finger
      framework
<221> NAME/KEY: SITE
<222> LOCATION: (1)..(2)
<223> OTHER INFORMATION: can be present or absent; Xaa = any amino acid
<221> NAME/KEY: SITE
<222> LOCATION: (4)..(8)
<223> OTHER INFORMATION: Xaa = any amino acid
<221> NAME/KEY: SITE
<222> LOCATION: (5)..(8)
<223> OTHER INFORMATION: can be present or absent
<221> NAME/KEY: SITE
<222> LOCATION: (10)..(23)
<223> OTHER INFORMATION: Xaa = any amino acid
<221> NAME/KEY: SITE
<222> LOCATION: (19)..(23)
<223> OTHER INFORMATION: can be present or absent
<221> NAME/KEY: SITE
<222> LOCATION: (25)..(30)
<223> OTHER INFORMATION: Xaa = any amino acid
<221> NAME/KEY: SITE
<222> LOCATION: (28)..(30)
<223> OTHER INFORMATION: can be present or absent
<221> NAME/KEY: SITE
<222> LOCATION: (31)
<223> OTHER INFORMATION: Xaa = His or Cys

<400> SEQUENCE: 4

Xaa Xaa Cys Xaa Xaa Xaa Xaa Xaa Cys Xaa Xaa Xaa Xaa Xaa Xaa Xaa
 1               5                  10                  15

Xaa Xaa Xaa Xaa Xaa Xaa Xaa His Xaa Xaa Xaa Xaa Xaa Xaa Xaa
            20                  25                  30
```

```
<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: zinc finger
      binding motif
<221> NAME/KEY: SITE
<222> LOCATION: (1)
<223> OTHER INFORMATION: Xaa = any amino acid
<221> NAME/KEY: SITE
```

```
<222> LOCATION: (3)..(6)
<223> OTHER INFORMATION: Xaa = any amino acid
<221> NAME/KEY: SITE
<222> LOCATION: (5)..(6)
<223> OTHER INFORMATION: may be present or absent
<221> NAME/KEY: SITE
<222> LOCATION: (8)..(10)
<223> OTHER INFORMATION: Xaa = any amino acid
<221> NAME/KEY: SITE
<222> LOCATION: (10)
<223> OTHER INFORMATION: may be present or absent
<221> NAME/KEY: SITE
<222> LOCATION: (12)..(16)
<223> OTHER INFORMATION: Xaa = any amino acid
<221> NAME/KEY: SITE
<222> LOCATION: (18)..(19)
<223> OTHER INFORMATION: Xaa = any amino acid
<221> NAME/KEY: SITE
<222> LOCATION: (21)..(23)
<223> OTHER INFORMATION: Xaa = any amino acid

<400> SEQUENCE: 5

Xaa Cys Xaa Xaa Xaa Xaa Cys Xaa Xaa Xaa Phe Xaa Xaa Xaa Xaa Xaa
 1               5                  10                  15

Leu Xaa Xaa His Xaa Xaa Xaa His
            20

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: linker

<400> SEQUENCE: 6

Thr Gly Glu Lys
 1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: linker

<400> SEQUENCE: 7

Thr Gly Glu Lys Pro
 1               5

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: consensus
      structure

<400> SEQUENCE: 8

Pro Tyr Lys Cys Pro Glu Cys Gly Lys Ser Phe Ser Gln Lys Ser Asp
 1               5                  10                  15

Leu Val Lys His Gln Arg Thr His Thr Gly
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: consensus
``` structure

<400> SEQUENCE: 9

Pro Tyr Lys Cys Ser Glu Cys Gly Lys Ala Phe Ser Gln Lys Ser Asn
 1               5                   10                  15

Leu Thr Arg His Gln Arg Ile His Thr Gly Glu Lys Pro
            20                  25

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: leader
      peptide

<400> SEQUENCE: 10

Met Ala Glu Glu Lys Pro
 1               5

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: plant
      translational initiation sequence

<400> SEQUENCE: 11
aaggagatat aacaatg                                              17

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: plant
      translational initiation sequence

<400> SEQUENCE: 12
gtcgaccatg                                                      10

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ctcctgcagt tggacctgtg ccatggccgg ctgggccgca tagaatggaa caactaaagc   60

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence:
      oligonucleotide target

<400> SEQUENCE: 14
aaaaaaggcg                                                      10

<210> SEQ ID NO 15
<211> LENGTH: 16

```
<212> TYPE: DNA
<213> ORGANISM: Artificial Sequence
<220> FEATURE:
<223> OTHER INFORMATION: Description of Artificial Sequence:
      oligonucleotide target

<400> SEQUENCE: 15
aaaaaaggcg aaaaaa                                                  16

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 16

Arg Ser Asp Glu Leu Thr Arg
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 17

Arg Ser Asp Asp Leu Ser Thr
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 18

Arg Ser Asp Asp Leu Ser Val
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 19

Arg Ser Asp Asp Leu Ser Gln
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 20

Thr Asn Asn Thr Arg Ile Lys
 1               5
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 21

His Lys Ala Thr Arg Ile Lys
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 22

Thr Asp Lys Val Arg Lys Lys
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 23

His Asn Ala Ser Arg Ile Asn
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 24

Thr Asn Asn Ser Arg Lys Lys
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 25

Thr Asn Ala Thr Arg Lys Lys
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

```
<400> SEQUENCE: 26

Thr Arg Asn Thr Arg Lys Asn
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 27

Thr Asn Asn Ser Arg Lys Asn
  1               5

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tataaaaaaa ggcgtgtcac agtcagtcca cacgtc                                  36

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
tataaaaaaa ggcgaaaaaa tcacagtcag tccacacgtc                              40

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 30

Arg Ser Asp Glu Leu Thr Arg His Ile Arg Ile His
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 31

Arg Ser Asp Thr Leu Ser Val His Ile Arg Thr His
  1               5                  10

<210> SEQ ID NO 32
<211> LENGTH: 12
<212> TYPE: PRT
<213> ORGANISM: Artificial Sequence
```

```
<220> FEATURE:
<223> OTHER INFORMATION: Description of Artificial Sequence: zinc finger
      binding domain

<400> SEQUENCE: 32

His Asn Ala His Arg Lys Thr His Thr Lys Ile His
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 33

Arg Ser Asp His Leu Ser Val His Ile Arg Thr His
 1               5                  10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 34

Lys Lys Phe Ala His Ser Ala His Arg Lys Thr His Thr Lys Ile His
 1               5                  10                  15

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
tatacaagct tggcgatcac agtcagtcca cacgtc                            36

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: DNA library
<221> NAME/KEY: misc_feature
<222> LOCATION: (7)
<223> OTHER INFORMATION: "n" is C or T
<221> NAME/KEY: misc_feature
<222> LOCATION: (8)
<223> OTHER INFORMATION: "n" is G or A
<221> NAME/KEY: misc_feature
<222> LOCATION: (9)
<223> OTHER INFORMATION: "n" is C or T
<221> NAME/KEY: misc_feature
<222> LOCATION: (10)
<223> OTHER INFORMATION: "n" is G or A
<221> NAME/KEY: misc_feature
<222> LOCATION: (11)
<223> OTHER INFORMATION: "n" is C or T

<400> SEQUENCE: 36
tatagtnnnn nggcgatcac agtcagtcca cacgtc                            36

<210> SEQ ID NO 37
```

```
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 37

Arg Ser Asp His Leu Ser Lys His Ile Arg Thr His
  1               5                  10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 38

Lys Lys Phe Ala Arg Ser Gln Thr Arg Ile Asn His Thr Lys Ile His
  1               5                  10                  15

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 39

Arg Ser Asp His Leu Ser Glu His Ile Arg Thr His
  1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 40

Thr Arg Asn Ala Arg Thr Lys His Thr Lys Ile His
  1               5                  10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 41

Arg Ser Asp His Leu Ser Asn His Ile Arg Thr His
  1               5                  10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 42
```

-continued

```
Arg Asn Asp Thr Arg Lys Thr His Thr Lys Ile His
 1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 43

```
Arg Ser Asp Asn Leu Ser Thr His Ile Arg Thr His
 1               5                   10
```

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 44

```
Lys Lys Phe Ala His Ser Asn Thr Arg Lys Asn His Thr Lys Ile His
 1               5                   10                  15
```

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
tatagttacg tggcgatcac agtcagtcca cacgtc                               36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
tatagttgta tggcgatcac agtcagtcca cacgtc                               36

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
tatagtcgta cggcgatcac agtcagtcca cacgtc                               36

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: DNA target

<400> SEQUENCE: 48
aaaaagcgga aaaa                                                    14

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 49

Gln Ser Arg Ser Leu Ile Gln
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 50

Gln Arg Asp Ser Leu Ser Arg
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 51

Arg Ser Asp Glu Arg Lys Arg
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 52

Arg Ser Asp Val Leu Ser Thr
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: zinc finger
      binding domain

<400> SEQUENCE: 53

Thr Arg Ser Ser Arg Lys Lys
 1               5

<210> SEQ ID NO 54
<211> LENGTH: 14
<212> TYPE: DNA
<213> ORGANISM: Artificial Sequence
<220> FEATURE:
<223> OTHER INFORMATION: Description of Artificial Sequence: operator

```
      site
<221> NAME/KEY: misc_feature
<222> LOCATION: (5)
<223> OTHER INFORMATION: "n" is G or T
<221> NAME/KEY: misc_feature
<222> LOCATION: (6)..(9)
<223> OTHER INFORMATION: "n" is A, C, G or T
<221> NAME/KEY: misc_feature
<222> LOCATION: (10)
<223> OTHER INFORMATION: "n" is A or T

<400> SEQUENCE: 54
acaannnnnn ttgt                                                   14

<210> SEQ ID NO 55
<211> LENGTH: 58
<212> TYPE: DNA
<213> ORGANISM: Artificial Sequence
<220> FEATURE:
<223> OTHER INFORMATION: Description of Artificial Sequence: target DNA
      sequence library
<221> NAME/KEY: misc_feature
<222> LOCATION: (28)..(31)
<223> OTHER INFORMATION: "n" is A, C, G or T

<400> SEQUENCE: 55
gtcggatcct gtctgaggtg agacaatnnn nattgtgtct tccgacgtcg aattcgcg    58

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: primer A

<400> SEQUENCE: 56
gtcggatcct gtctgaggtg ag                                          22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: primer B

<400> SEQUENCE: 57
cgcgaattcg acgtcggaag ac                                          22

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: operator
      sequence

<400> SEQUENCE: 58
acaataaata ttgt                                                   14

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: plant
      translational initiation sequence

<400> SEQUENCE: 59
aaggagatat aaca                                                   14
```